United States Patent [19]

Young

[11] Patent Number: 5,200,345

[45] Date of Patent: Apr. 6, 1993

[54] METHODS AND APPARATUS FOR QUANTIFYING TISSUE DAMAGE, DETERMINING TISSUE TYPE, MONITORING NEURAL ACTIVITY, AND DETERMINING HEMATOCRIT

[75] Inventor: Wise Young, New York, N.Y.

[73] Assignee: New York University, New York, N.Y.

[21] Appl. No.: 561,986

[22] Filed: Aug. 2, 1990

Related U.S. Application Data

[63] Continuation-in-part of Ser. No. 394453, Aug. 16, 1989, abandoned.

[51] Int. Cl.$^5$ .................... G01N 33/48; G01N 33/86; G01N 21/00; A61B 5/05
[52] U.S. Cl. ........................................ 436/63; 436/70; 436/79; 436/173; 422/68.1; 422/82.03; 128/653.1; 128/653.2; 324/317
[58] Field of Search ............... 436/83, 64, 74, 79, 436/164, 70; 422/68.1, 82.03; 128/653 R, 653 A, 639, 653.1, 653.2; 324/316, 317, 318

[56] References Cited

U.S. PATENT DOCUMENTS

| 4,663,289 | 5/1987 | Veech | 435/2 |
| 4,742,304 | 5/1988 | Schnall et al. | 324/318 |
| 4,779,619 | 10/1988 | Winkler | 128/653 A |
| 4,849,362 | 7/1989 | DeMarinis et al. | 436/63 |
| 4,870,024 | 9/1989 | Musacchio et al. | 436/74 |

FOREIGN PATENT DOCUMENTS

| 2-59669 | 2/1990 | Japan | 436/74 |
| 1291873 | 2/1987 | U.S.S.R. | 436/74 |

OTHER PUBLICATIONS

"Pathologic Basis of Disease", Robbins, W. B. Saunders Co., Philadelphia, Pa., 1974, pp. 314-315.
"Textbook of Clinical Chemistry", Tietz et al. (eds), W. B. Saunders Co, Philadelphia, Pa., 1986, pp. 1173-1183, 1248-1251.

Primary Examiner—James C. Housel
Assistant Examiner—N. Bhat
Attorney, Agent, or Firm—Browdy and Neimark

[57] ABSTRACT

Tissue damage may be quantified, tissue type identified, neural activity monitored or blood hematocrit determined by measuring the difference between the total tissue sodium and potassium concentrations in the area in question. Comparison of these measurements with standard values permit evaluation of the amount of tissue damage in cells of the same type or the tissue type in non-necrotic cells. Evaluation over time of normal brain cells permit monitoring of neural activity. By directly and simultaneously measuring sodium and potassium ion concentrations, for example, a nuclear magnetic resonance spectrometer can image areas of different tissue type in differing colors. In this manner tumors and lesions can be clearly delineated. Measurement of total potassium concentration of a blood sample and the potassium concentration of the cell-free plasma will permit determination of cellular volume fraction (hematocrit).

36 Claims, 7 Drawing Sheets

METHODS AND APPARATUS FOR QUANTIFYING TISSUE DAMAGE, DETERMINING TISSUE TYPE, MONITORING NEURAL ACTIVITY, AND DETERMINING HEMATOCRIT

CROSS-REFERENCE TO RELATED APPLICATION

The present application is a continuation-in-part of serial no. 07/394,453, filed Aug. 16, 1989, now abandoned, the entire contents of which are hereby incorporated herein by reference.

FIELD OF THE INVENTION

The present invention relates to methods for quantifying tissue damage, determining tissue type or monitoring neural activity by analyzing the concentrations of sodium ion and potassium ion in tissue, determining the cell volume of blood (hematocrit), and determining extent of blood loss and dehydration. The present invention further relates to methods and apparatus for measuring the relative sodium and potassium ion concentration of tissue.

BACKGROUND OF THE INVENTION

Biologists and clinicians are constantly faced with the problem of assessing tissue damage; currently available methods are cumbersome and often not accurate. Pathologists devote a great deal of time to examining the histology of tissues, counting cells, and estimating tissue damage from the subjective appearance of cells. Radiologists spend a majority of their time trying to find pathological changes on X-rays or magnetic resonance images which would indicate tissue damage. Surgeons rely primarily on visual clues to judge what tissues to remove and what tissues to save, which is not an accurate method of assessing damage, as living tissues often look dead. Additionally, surgeons currently cannot be certain that all diseased tissue is removed during a surgical procedure, which presents a great problem when malignant tissue is being removed.

Even in the laboratory, there is no reliable method for quantifying tissue damage. Investigators spend millions of dollars on tracers and spend months counting cells to measure tissue damage. In order to save time, many investigators simply measure gross areas of necrosis. Since it is not always possible to determine visually which cells are living and which cells are dead, nor the extent of tissue damage to an organ, the currently available methods can be described as crude, at best.

The relative sizes of extracellular and intracellular space in tissue is a valid estimation of the amount of tissue damage in the total space measured. Normal brain tissue, for example, generally has an intracellular volume fraction of about 90%. If tissue is damaged, the intracellular compartments of the dead cells equilibrate with the extracellular space and thus the intracellular volume fraction will drop. The smaller the intracellular volume fraction, the greater the amount of damage in the sample.

The relative sizes of extracellular and intracellular space in brain tissues have been the focus of many scientific studies. Many ingenious methods have been devised to make this determination. In the 1960's, two methods were dominant. One method involved passing an electric current through brain tissues. Because the cells are relatively impervious to electrical currents, the impedance of the brain tissues gave a rough indication of the relative size of the extracellular space. The second method involved the use of macromolecular tracers, including soaking tissue in solutions of these tracers and then measuring the concentration of the substance in the tissue. The ratio of the tissue concentration to the medium was then determined to indicate the space occupied by the tracer.

The tracer methods suffered from several drawbacks. No tracer substance is ideal, and all tracers penetrate into the cells to some degree. Different tracers yield different values of extracellular space. Delivery of the tracer into the tissue is problematical. If the tracer is administered intravenously, its penetration into the brain tissues may be limited by the blood-brain barrier. Blood flow also influences delivery. Therefore, to interpret the data, multiple tracers are necessary: one to monitor blood-brain barrier breakdown, one to measure blood flow, and one to assess extracellular space.

C. Nicholson at New York University developed a method for measuring extracellular volume fraction ($V_e/V_t$) by introducing a tracer substance such as tetraethylammonium (TEA), which should not penetrate the cells. If the extracellular volume increases or decreases, the concentration of TEA changes. By measuring the concentration of TEA with microelectrodes, it is possible to estimate $V_e/V_t$. The intracellular volume, $V_i$, divided by $V_t$, is equal to $1 - V_e/V_t$. This method also has several major disadvantages. First, it is quite difficult to introduce tracer substances into tissues. The tracer concentration in extracellular space must first be measured before a given injurious event, and then the change must be observed. It is difficult to ensure that the same amount of tracer is injected into the tissue. Second, the method gives the extracellular volume fraction only in the immediate vicinity of the microelectrode recording. Since the ratio of the extracellular volume to the tissue volume may vary within the tissue, it is necessary to sample many points of tissue in order to obtain a representative average value. Thirdly, the ion-selective microelectrodes required to measure the tracer concentrations are fragile and difficult to make. Fourthly, the equations for calculating the extracellular volume fraction require a factor called tortuosity, the convolutions of the pathways through which the ions must diffuse. This factor is resolvable by assuming that the tissue is anisotropic, i.e., that the diffusion of ions is the same in all directions. This method is not accurate when applied to tissues with oriented cellular structures, such as white matter. Because of the complexity of this method, the measured values must be checked very carefully, and errors can very easily arise.

Accordingly, a relatively simple and accurate method of determining intracellular volume fraction has been long sought in order to quantify the extent of tissue damage in any given tissue sample.

Another problem facing biologists and clinicians is obtaining accurate imaging of different types of soft tissue. Existing imaging technology, such as x-ray and NMR, depend on tissue density or differences in proton relaxation rates to identify different tissue types. Both tissue density and proton concentrations have one major drawback. Neither directly reflect tissue damage or biological changes in the tissue. For example, tissue density to x-rays depends on the concentration of x-ray absorbing substances, such as calcium. Calcium concentrations do not change much in acutely injured soft tissues and, if they do change, take place over a period of days, weeks, or months. X-rays, therefore, are primarily useful for visualizing bone and detecting chronic soft tissue injuries. Likewise, magnetic resonance signals resulting from proton relaxation times in tissues represent complex and yet poorly understood contributions from hydrogen in water and organic substances. While magnetic resonance signals do change relatively rapidly in injured tissue, thus allowing early detection and imaging of tissue changes, the nature of the changes is not well understood. Furthermore, the signal changes are relatively small and not necessarily linearly related to known tissue variables. Thus, accurate imaging and differentiation of tissue damage, tumors, and normal tissues of different organs are limited with current technology.

The measurement of neural activity is a very important area of brain research. Presently, this must be done with external or implanted electrodes. There are many disadvantages to such techniques. A non-invasive technique for imaging changes in neural activity in different portions of the brain would be an invaluable research tool.

Probably the most common blood test utilized by clinicians and others is the hematocrit or measurement of cell volume in blood. The present techniques for measuring hematocrit are relatively crude and involve centrifugation of whole blood in a glass capillary tube until the cells are packed at the bottom. The ratio of the cells to total blood volume represents the hematocrit. Most instruments measure hematocrit by optically measuring the heights of the different phases of centrifuged blood. Several disadvantages are associated with this procedure for measuring hematocrits.

1. The instruments required for centrifugation of the capillary tubes and optical measurements tend to be bulky and cannot be easily run on battery. Therefore, portable hematocrit machines are not readily available.

2. The accuracy of hematocrits depends critically on the absence of blood clotting and lysis. If the blood cells were to clot or lyse, the hematocrit becomes grossly inaccurate. Thus, it is essential that the blood be relatively fresh, be placed in a container immediately with anticoagulants, and be centrifuged under appropriate conditions.

3. Hematocrits are relatively imprecise. Most hematocrits measured by eye, using a modified ruler scale, probably are no more accurate than $\pm 5\%$ of the mean, e.g., 2% of the normal 40% hematocrit. Factors such as centrifugation force and time, packing of the cells, etc., also may play a role in the variability of measurements.

A quick and accurate test for determining hematocrit in any blood sample, including clotted blood, lysed blood and even blood from corpses, which can be implemented with a small portable device, would be a very valuable addition to the hematological analytical array.

SUMMARY OF THE INVENTION

It is an object of the present invention to overcome the above-mentioned deficiencies in the prior art.

It is another object of the present invention to provide a method for determining the amount of living and/or dead tissue in a tissue sample and quantifying the relative amount of damage in that sample.

It is yet another object of the present invention to provide a method for distinguishing different types of living tissue.

A further object of the present invention is to provide a method to determine neural activity in the central nervous system.

It is yet another object of the present invention to provide a method to give substantially instant feedback to a surgeon as to the relative amount of tissue damage or the type of tissue being removed as it is being removed.

It is still another object of the present invention to provide a non-invasive imaging technique to show the amount of tissue damage in the tissue areas being scanned.

It is a further object of the present invention to provide a quick and accurate test for determining hematocrit and extent of blood loss or dehydration using small portable equipment.

It is yet a further object of the present invention to provide a direct measure method for determining hematocrit which is easier and more precise than the standard centrifugation approaches to determining hematocrit and can be applied to any blood removed from the body even after it has clotted and lysed.

It is a further object of the present invention to provide apparatus for carrying out all of said methods.

According to the present invention, tissue damage may be quantified in damaged tissue of the same type, tissue type can be determined in tissue which is not necrotic, neural activity can be monitored, and blood hematocrit can be determined, all by the simple expedient of measuring the difference in the total sodium and potassium ion concentrations in the tissue sample, sometimes with the additional expedient of measuring the sodium and/or potassium ion concentrations in the extracellular fluid, such as CSF or blood plasma. The present invention is based on the realization of a mathematical formula which establishes that the difference in the total sodium and potassium ion concentrations in tissues is linearly related to the volume of cytoplasm in the tissue with a slope reflecting the average transmembrane cationic gradient and a y-intercept reflecting the difference in extracellular sodium and potassium concentrations. Since the value of the average transmembrane cationic gradient is relatively constant in a given tissue type, and this constant value is known, the difference in the total sodium and potassium ion concentrations in the tissue sample will be directly related to the intracellular volume fraction. Thus, by merely measuring the total sodium ion concentration and the total potassium ion concentration in a tissue sample, one has a relative indication of intracellular volume fraction which in turn is an accurate indication of the volume of living cells in the tissue. By comparing to a normal control and assigning a constant normal transmembrane cationic gradient for the particular tissue type being examined, a special case of average intracellular volume fraction can be accurately determined. In such a case, the difference in total tissue sodium and potassium concentrations is linearly related to a value of intracellular volume fraction representing the equivalent volume of cytoplasm with normal transmembrane cationic gradient or the idealized intracellular volume fraction of the tissue (IVF*). This idealized intracellular volume fraction approximates the volume of living cells in the tissue.

It is further known that cells of different tissue types or in different states, such as normal cells versus malignant cells, or muscle cells versus liver cells, etc., have substantially constant average intracellular volume fractions but have different average cellular transmembrane cationic gradients. If the intracellular volume fraction is considered to be constant, changes in the difference between total sodium and potassium ion concentrations will represent changes in the average cellular transmembrane cationic gradients and, thus, changes in tissue type. If the total tissue sodium and potassium ion concentrations are measured by the device, such as, for example, by means of nuclear magnetic resonance spectroscopy, the device will image areas of different average cellular transmembrane cationic gradients. Measurements based on the assumption of constant intracellular volume fraction will yield differences in average transmembrane cationic gradients or G*.

Furthermore, in normal brain tissues over short time periods, where the intracellular volume fraction and the transmembrane cationic gradient remain relatively constant, differences in tissue sodium and potassium ion concentration will reflect neural activity since brain activity causes sodium and potassium movements and the difference in tissue sodium and potassium concentrations will reflect these movements accordingly. Thus, the device can be used to detect and measure neural activity.

Previously, the cellular volume fraction or hematocrit of blood was determined by a centrifugation method using calibrated capillary tubes. Data has now been obtained showing that a formula involving the measurements of only whole blood potassium concentrations ($[K]_t$) and extracellular or plasma potassium concentrations ($[K]_e$) is a robust and accurate indicator of blood hematocrit. $[K]_t$ and $[K]_3$ measurements are easier and more precise than the standard centrifugation approaches to determining hematocrit and can be applied to any blood removed from the body, even after it has clotted and lysed. In addition, whole blood sodium concentration ($[Na]_t$) and $[K]_t$ measurements provide an estimate of blood ionic osmolarity, an important indicator of dehydration which will aid interpretation of hematocrit and $[Na]_t$ and $[K]_t$ changes. Finally, measuring hematocrit (in the standard manner), and performing linear regression analysis of $[Na]_t-[K]_t$ versus hematocrit will provide a quantitative estimate of the difference between extracellular sodium ($[Na]_e$) and $[K]_e$ from the y-intercept of regression, as well as the average ionic gradient across blood cell membranes (G) from the slope of the regression. This forms the basis of a new method of measuring hematocrit that can be easily implemented in small portable devices.

Sodium and potassium ion concentration can be measured by any applicable technique. For example, potassium and sodium ion sensitive microelectrodes can be used as can atomic absorption spectrophotometry, flame photometry, ionic titration or nuclear magnetic resonance spectroscopy.

The present invention will be better understood from a consideration of the following detailed description of the preferred embodiments and the brief description of the drawings.

DETAILED DESCRIPTION OF THE INVENTION

Figure 1:
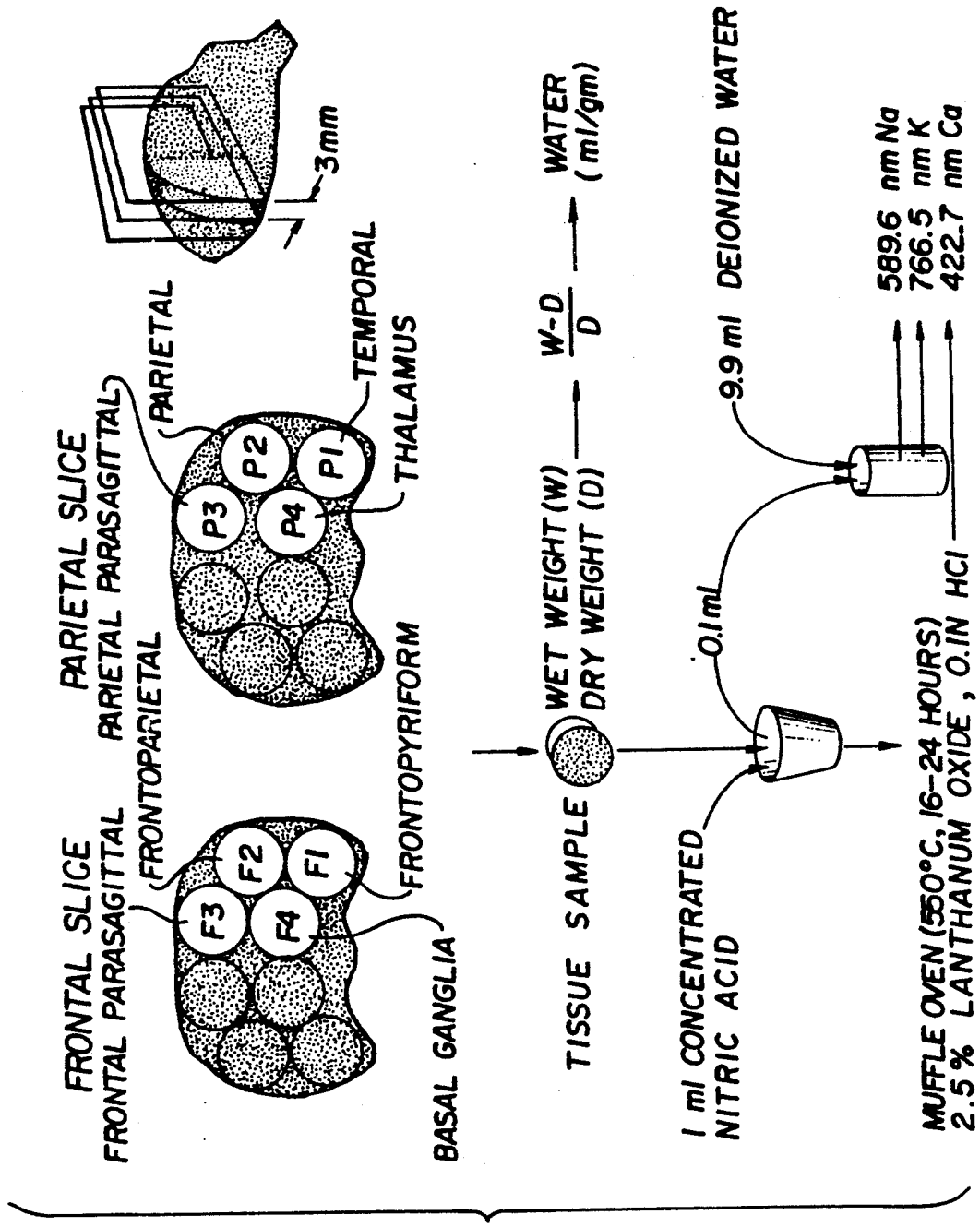
FIG. 1 shows the procedure for measuring tissue sodium and potassium concentrations in rat brains after cerebral ischemia produced by occlusion of the middle cerebral artery.

Sodium and potassium ions constitute more than 98% of the positively charged inorganic ions in mammalian tissues. Together, these ions account for more than 99% of the osmotic activity of the tissue. Small cationic gradients cause enormous osmotic forces. For example, a 10 mM difference in Na+K concentrations will generate more than 1 atmosphere of pressure, i.e., 760 mm Hg compared to only 100–200 mm Hg exerted by the blood pressure. Water will shift to reduce osmotic gradients, due to pressures that are generated. Therefore, we can reasonably assume that the sum of Na and K concentrations in different compartments of tissue are equal, i.e., $$[Na]_t+[K]_t=[Na]_e+[K]_e=[Na]_i+[K]_i \qquad (1)$$

where $[Na]_t$ and $[K]_t$ are the tissue concentrations of sodium and potassium, $[Na]_e$ and $[K]_e$ are the extracellular sodium and potassium concentrations, and $[Na]_i$ and $[K]_i$ are the intracellular concentrations of sodium and potassium, respectively. Shifting these terms, we arrive at:

$$[Na]_i-[Na]_e=[K]_e-[K]_i=G \qquad (2)$$

where G represents the sodium and potassium cationic gradients across cellular membranes. We know that the sum of cationic contents of intracellular and extracellular compartments is equal to the total cationic contents, i.e., $$[Na]_t V_t=[Na]_i V_i+[Na]_e V_e \qquad (3)$$

and $$[K]_t \cdot V_t = [K]_i \cdot V_i + [K]_e \cdot V_e \quad (4)$$

where $V_e$, $V_i$ and $V_t$ are the volumes of the extracellular and intracellular compartments and the total tissue volume, respectively. Subtracting equation (4) from equation (3) gives:

$$([Na]_t - [K]_t) \cdot V_t = ([Na]_i - [K]_i) \cdot V_i + ([Na]_e - [K]_e) \cdot V_e \quad (5)$$

From equation (2), it is known that $[K]_i = [K]_e - G$ and $[Na]_i = G + [Na]_e$. Substituting this into equation (5) gives:

$$([Na]_t - [K]_t) \cdot V_t = ([Na]_i - [K]_i) \cdot (V_i + V_e) + 2G \cdot V_i / V_t \quad (6)$$

Dividing both sides of the equation by $V_t$ and knowing that $V_t = V_i + V_e$, one can arrive at the following equation:

$$([Na]_t - [K]_t) = ([Na]_e - [K]_e) + 2G \cdot V_i / V_t \quad (7)$$

By using equation (7) above, it can be seen that the difference between tissue sodium and potassium concentrations relates linearly to the ratio of intracellular to total tissue volumes ($V_i/V_t$) with a y-intercept of ($[Na]_e - [K]_e$) and a slope that is twice the cationic gradient across membranes (G). Since $V_i$ is the volume of the intracellular compartment and $V_t$ is the tissue volume, $V_i/V_t$ is the intracellular volume fraction. G is the gradient of sodium or potassium across the cellular membranes. $[Na]_e$ and $[K]_e$ can be measured, e.g. with ion-selective microelectrodes, or can be assumed to have equilibrated with plasma or cerebrospinal fluid. $[Na]_e$ and $[K]_e$ should equilibrate with plasma values rapidly, within hours, due to ionic diffusion. By assuming that $[Na]_e - [K]_e$ is equal to plasma $[Na] - [K]$, either G or $V_i/V_t$ can be estimated from the equation. If G is measured or assumed to be normal, $V_i/V_t$ can be determined. Conversely, if $V_i/V_t$ is measured or assumed to be normal, G can be determined. Similarly, if $[Na]_e - [K]_e$ and G are substantially constant when $[Na]_t - [K]_t$ is being measured, such as in chronically injured tissues, $[Na]_t - [K]_t$ is directly related to $V_i/V_t$. If $[Na]_e - [K]_e$ and $V_i/V_t$ are substantially constant when the $[Na]_t - [K]_t$ changes are being measured, as when there is no substantial cell loss in the tissue and the tissue type is being determined, $[Na]_t - [K]_t$ is directly related to G.

The value of $V_i/V_t$ is intracellular volume fraction. Intracellular volume fraction should approximate the cellular volume fraction, i.e., the volume of cells divided by total tissue volume. When the "tissue" being studied is blood, the cellular volume fraction is also known as the hematocrit of the blood. Solving equation (7) for $V_i/V_t$ gives the following equation:

$$V_i/V_t = (([Na]_t - [K]_t) - ([Na]_e - [K]_e))/2G \quad (8)$$

Thus, measurement of $[Na]_t - [K]_t$ provides a value directly related to the cellular volume fraction. In other words, there is a linear relationship between the difference in total Na and K concentrations and the cellular volume fraction.

The number of measurements necessary to solve equation (8) can be decreased in view of the relationship of equation (1), i.e., $[Na]_t + [K]_t = [Na]_e + [K]_e$. Solving for $[Na]_e$ we arrive at:

$$[Na]_e = [Na]_t + [K]_t - [K]_e \quad (9)$$

Substituting equation (9) into equation (8) yields a much simpler equation:

$$V_i/V_t = ([K]_e - [K]_t)/G \quad (10)$$

Thus, assuming a normal value for transmembrane ionic gradient (G), only the potassium concentration of the total homogenized tissue and the potassium concentration of the cell-free fluid need be measured to determine a substantially accurate value for cellular volume fraction. This greatly simplifies the apparatus necessary to determine hematocrit since only a potassium selective electrode need be present with no measurement of sodium being necessary.

It is also possible to assume a normal value for $[K]_e$ and thus obtain a substantially accurate cellular volume fraction measurement by measuring only the total potassium ion concentration. If $[K]_e$ and (G) are normal, i.e., 5 mM and $-124$ mM, respectively, then $$V_i/V_t = (5 - [K]_t)/-124 = ([K]_t - 5)/124 \quad (11)$$

$[K]_e$ usually remains constant in biological tissues whereas $[Na]_e$ can vary greatly. Normal $[Na]_e$ values vary within a range of 130–160 mM whereas $[K]_e$ is always tightly controlled in the range of 3–5 mM. The reason is because biological tissues cannot tolerate large fluctuations of $[K]_e$. Furthermore small $[K]_e$ changes have profound effects on membrane potentials. Electrochemical potentials can be calculated from the Nernst equation, where $E_m$ is the transmembrane potential recorded with an electrode inserted into a cell (relative to a reference electrode outside the cell), z is the valence of the ion, R is the Universal Gas Constant, F is Faraday's constant and T is the temperature in absolute (Kelvin) degrees:

$$E_m = \frac{RT}{zF} \log \frac{[Ion]_i}{[Ion]_e} \quad (12)$$

If $G = -125$ mM, where $[K]_e$, $[K]_i$, $[Na]_e$, and $[Na]_i$ are 4, 129, 150, and 25 mM respectively, the ionic gradients will have the following Nernst potentials.

$$E_{Na} = -63 \log \frac{[Na]_i}{[Na]_e} = +49 \text{ mV} \quad (13)$$

$$E_K = -63 \log \frac{[K]_i}{[K]_e} = -94 \text{ mV} \quad (14)$$

Thus, a 5 mM increase in $[K]_e$, for example, produces a 25 mV change in $E_K$ whereas a 5 mM increase in $[Na]_e$ would change $E_{Na}$ by $<1$ mV. $[K]_e$ levels exceeding 10 mM are incompatible with neuronal, muscle, and cardiac activity.

Since $[K]_e$ stays within a narrow range in the tissues, we can reasonably assume normal values of $[K]_e$ in uninjured tissues or injured tissues that have had time to equilibrate with plasma. In any case, since $[K]_e$ is usually much smaller than $[K]_t$, small deviations of $[K]_e$ from assumed values will introduce only minor errors in the estimates of $V_i/V_t$. $[K]_e$ can also be approximated from measurement of cerebrospinal fluid or blood $[K]_e$. The former can be imaged in the ventricles of the brain. $[K]_e$ can be easily determined by chemical analysis from both CSF and blood samples.

When dealing with blood, the sum of the sodium and potassium concentration measurements provide an estimate of blood ionic osmolarity, an important indicator of dehydration which will aid interpretation of hematocrit changes.

Direct measurements of transmembrane ionic gradient are usually difficult because intracellular ionic concentrations cannot be readily determined with ion-selective microelectrodes or other means. Penetration of a cell, for example, with a microelectrode will allow leakage of extracellular fluids into the cells. Moreover, it is difficult to measure transmembrane ionic gradients in a large number of cells. The following equation provides a simple and easy method of estimating the average transmembrane ionic gradients of cells in any given tissue.

$$G = \frac{([Na]_t - [K]_t) - ([Na]_e - [K]_e)}{2(V_i/V_t)} \quad (15)$$

G can be accurately determined by measuring $[Na]_t-[K]_t$, $[Na]_e-[K]_e$ and $V_i/V_t$. G can also be estimated from $[Na]_t-[K]_t$ and $V_i/V_t$ alone by use of linear regression without measuring $[Na]_e-[K]_e$. The slope of regression gives 2·G. G may be a useful clinical diagnostic parameter.

It is important to accurately define the various terms used in the above-described relationships, to assess sources of error in the measurement thereof, and to control the extent of any such error as much as possible. The equations refer to intracellular $(V_i)$, extracellular $(V_e)$, and total tissue $(V_t)$ volumes. Because tissues are inhomogeneous and may contain substantive non-aqueous (e.g., lipid) compartments which have less or no ions, $V_t$, $V_i$, and $V_e$ may not necessarily relate exactly to the actual volumes of two compartments in the tissue. Furthermore, the ionic concentration terms are subject to different definitions. Because Na and K may be bound and concentrations can be expressed as a function of volume, tissue weight, or other denominators, application of the equation may lead to misleading values of $V_i/V_t$, depending on how they are measured and defined. Accordingly, the following definitions are intended throughout the present specification and claims.

$V_i$ and $V_e$ are the spaces in which Na, K, and water are distributed inside and outside cells and $V_t=V_i+V_e$. These spaces are clearly theoretical entities excluding compartments to which Na and K cannot diffuse and partially including compartments to which Na and K have limited access. $[Na]_i$, $[K]_i$, $[Na]_i$, $[K]_i$, $[Na]_e$, and $[K]_e$ are the concentrations of free Na or K in each of these spaces. Note that free ionic concentration is not the same as ionic activity. Ionic activity is concentration dependent whereas free ionic concentration represents the amount in solution and capable of exerting osmotic force.

Measurement and expression of tissue concentrations can introduce two types of errors in $V_i/V_t$ calculations. The first source of error is that ionic measurements may not reflect free ionic concentrations. For example, atomic absorption spectroscopy detects all Na or K in the tissue regardless of their binding state. While Na and K are highly soluble ions, some Na and K may be bound or precipitated. Atomic absorption thus tends to overestimate free ionic concentrations, with a $[Na]_t-[K]_t$ that is higher than it should be, and a $V_i/V_t$ that is smaller than it should be. Some methods, such as ion-selective electrodes, measure ionic activity which is typically less than free ion concentrations. Other methods that depend on radiated signals, such as magnetic resonance and fluorescence from tracers, will underestimate ionic concentrations because signal may be absorbed or shielded from detectors. Ion-selective electrodes and radiated signal measurements often result in smaller $[Na]_t-[K]_t$ and larger $V_i/V_t$ values.

The second source of error stems from the denominators of the ionic concentration terms. For example, $[Na]_t-[K]_t$ is expressed in $\mu$mol/gm wet tissue weight (W). Wet tissue weights represent all the materials present in the tissue, including non-aqueous compartments where Na and K cannot effectively distribute. Although the magnitude of the error depends on tissue composition, the general effect is for an underestimation of $[Na]_t-[K]_t$ and consequently $V_i/V_t$ values that are larger than they should be. In some tissues, such as liver, as much as 20% may be occupied by fat. This can result in a gross overestimation of $V_i/V_t$. Note that this error would occur even if the concentration terms were expressed as a function of actual tissue volume.

Fortunately, both sources of errors have relatively small effects on experimental results for two reasons. First, various sources of error balance each other. For example, atomic absorption spectroscopic measurements overestimate $[Na]_t-[K]_t$ while the expression of the concentrations in units of $\mu$mol/g underestimate $[Na]_t-[K]_t$. Thus, the measured values will approach the actual tissue concentrations. Second, any systematic error affecting both Na and K measurements will have less effect on $V_i/V_t$ than one might expect. For example, if measured $[K]_t=110$ mM and $[Na]_t=55$ mM, and it is assumed that $[K]_e=4$ mM, $[Na]_e=150$, and $G=-124$ mM, then $V_i/V_t=0.81$. If both K and Na were actually 10% less than measured, i.e., $[Na]_t-[K]_t=-50$ mM and the same $[Na]_e$, $[K]_e$, and G values, $V_i/V_t$ falls to 0.79, a difference of only 0.02.

In situations where tissues can be removed and analyzed for $[Na]_t-[K]_t$, our data indicates that $[Na]_t-[K]_t$ values accurately predict $V_i/V_t$. However, in clinical situations where non-invasive methods are being used to detect $[Na]_t-[K]_t$, ambiguous values of $[Na]_t-[K]_t$ may result from instrumentation or technological limitations. For example, magnetic resonance measurements of Na and K do not detect all the Na and K in the tissue. For this reason, it is paramount that an effective method be developed to ensure and to monitor the accuracy of $[Na]_t-[K]_t$ measurements. This can be easily done if the initial assumption is simply extended one step further to state that the sum of Na and K concentrations is the same in tissue as Na and K concentrations in plasma, i.e., $$[Na]_i+[K]_i=[Na]_e+[K]_e=[Na]_t+[K]_t=[Na]_p+[K]_p \quad (16).$$

$[Na]_p+[K]_p$ should closely approximate actual Na and K concentrations. Note that cerebrospinal fluid can be used for the same purpose in the case of nervous tissues.

This assumption provides an elegant way of evaluating and normalizing tissue ionic measurements. If $[Na]_{tm}$ and $[K]_{tm}$ are measured total tissue Na and K concentrations and $$P = \frac{[Na]_{tm} + [K]_{tm}}{[Na]_p + [K]_p} \quad (17)$$

then $$[Na]_t = [Na]_{tm} \cdot P \quad (18)$$

$$[K]_t = [K]_{tm} \cdot P \quad (19)$$

$$[Na]_t - [K]_t = ([Na]_{tm} - [K]_{tm}) \cdot P \quad (20)$$

and $$V_i/V_t = \frac{[K]_e - P \cdot [K]_{tm}}{G} \quad (21)$$

Some errors may result from normalization of tissue ionic concentrations. The normalization procedure assumes that the causes of $[Na]_t$ or $[K]_t$ deviations applies equally to both Na and K. This may not be true if one ion is affected more than the other. If more Na is bound than K, i.e., $[Na]_{tm} > [Na]_t$ and $[Na]_{tm} - [K]_{tm} > [Na]_t - [K]_t$, normalization would compound this error by making $[Na]_{tm} - [K]_{tm}$ even larger. However, normalization will bring $[Na]_{tm} - [K]_{tm}$ closer to $[Na]_t - [K]_t$ if significantly more K is bound than Na. In such a case, $[K]_{tm}$ overestimates actual $[K]_t$ values and $[Na]_{tm} - [K]_{tm}$ underestimates $[Na]_t - [K]_t$. Since $[Na]_{tm} + [K]_{tm} > [K]_p$ and $P > 1$, normalization would appropriately increase $[Na]_t - [K]_t$. Thus normalization will result in errors only if $[Na]_{tm}$ is selectively reduced compared to $[K]_{tm}$ and normalization will help if $[K]_{tm}$ selectively reduced.

The advantages of normalization far outweigh any error that may arise from normalization. First, normalizing $[Na]_{tm} - [K]_{tm}$ will adjust concentration values to reflect free ionic concentrations and reduce variability due to inaccurate volume denominators in the concentration terms. Such concentration an volume errors are likely to contribute much greater deviations of $V_i/V_t$ than differences in Na and K binding. For example, fatty tissues may have $[Na]_{tm} + [K]_{tm}$ values that are 20-30% smaller than $[Na]_p + [K]_p$. Second, the normalization utilizes an internal control. $[Na]_t + [K]_t$ in the plasma or cerebrospinal fluid of each individual serves as the normalizing factor. Plasma samples can be easily drawn and analyzed. In brain imaging applications, P can be determined from the ratios of [Na]+[K] signals in cerebral ventricular fluids. Third, normalization allows measured Na and K signals to be in any form so long as they are linearly related to Na and K concentrations. Normalization will reduce instrumentation errors.

One of the strengths of the $[Na]_t - [K]_t$ equation is its universality. It can be applied to any tissue with cells, Na, K, and water. We have already shown that $[Na]_t - [K]_t$ predicts CVF in injured spinal cords and blood. It is of interest to determine if the equation is applicable to other tissues. We therefore measured $[Na]_{tm} - [K]_{tm}$ and estimated $V_i/V_t$ in a wide variety of tissues. Table 1 lists the results. The column labelled CVF represents the $V_i/V_t$ values calculated from normalized $[Na]_{tm} - [K]_{tm}$ values.

TABLE 1

Cell Volume Fractions in Normal Rat Tissues

| Sample Site | $[Na]_{tm} + [K]_{tm}$ | $[Na]_{tm} - [K]_{tm}$ | $V_i/V_t$ | CV | n |
|---|---|---|---|---|---|
| Frontopyriform cortex | 172.6 ± 8.8 | −65.2 ± 3.1 | 0.94 ± 0.04 | 0.85 ± 0.01 | 10 |
| Lateral parietal cortex | 170.8 ± 9.4 | −63.9 ± 6.5 | 0.94 ± 0.06 | 0.85 ± 0.02 | 10 |
| Parasagittal cortex | 169.1 ± 7.5 | −54.9 ± 4.5 | 0.87 ± 0.03 | 0.82 ± 0.02 | 10 |
| Thalamus | 164.9 ± 5.7 | −59.4 ± 4.5 | 0.86 ± 0.03 | 0.84 ± 0.01 | 10 |
| Thoracic spinal cord | 164.0 ± 7.3 | −18.5 ± 8.0 | 0.70 ± 0.04 | 0.68 ± 0.03 | 50 |
| Liver | 132.3 ± 4.3 | −68.2 ± 4.3 | 0.80 ± 0.03 | 0.91 ± 0.02 | 9 |
| Heart (ventricles) | 137.1 ± 11.0 | −38.5 ± 7.2 | 0.70 ± 0.06 | 0.76 ± 0.03 | 9 |
| Kidney | 149.6 ± 7.7 | −3.4 ± 8.1 | 0.60 ± 0.03 | 0.60 ± 0.03 | 9 |
| Lung | 164.1 ± 8.8 | −1.1 ± 7.9 | 0.66 ± 0.06 | 0.59 ± 0.03 | 9 |

Explanation:
$[Na]_{tm} + [K]_{tm}$ and $[Na]_{tm} - [K]_{tm}$ are respectively the sum and difference in tissue Na and K concentrations expressed in units of μmol/g wet tissue. $V_i/V_t$ were calculated from $([K]_{tm} - 4)/124$. CVF were calculated from $(([K]_{tm} \cdot P) - 4)/214$ where P is the ratio of $([Na]_{tm} + [K]_{tm})/([Na]_p + [K]_p)$ and $[Na]_p + [K]_p$ is the sum of Na and K concentrations in plasma from individual animals. Standard deviations are given.

$[Na]_{tm} + [K]_{tm}$ varied significantly from tissue to tissue, suggesting the need to normalize the values of $[Na]_p + [K]_p$. The normalized CVF values are reasonable approximations of expected CVF values in the tissues. In brain, CVF ranged from 0.82 to 0.85. Spinal cord CVF is much lower at 0.68. Liver appears to be the most cellular of all the tissues examined with a CVF of 0.91. Heart and lung are less cellular with CVF values of 0.76 and 0.60. Kidney tissues, because of the presence of vasculature and tubules, are the least cellular of the tissues examined.

The data supports the importance and beneficial effects of normalizing $[Na]_{tm} - [K]_{tm}$ in two ways. First, the normalized CVF values are close to expected values while uncorrected $V_i/V_t$ values occasionally give unreasonable values. For example, uncorrected $[Na]_{tm} - [K]_{tm}$ of cerebral cortical tissues suggest $V_i/V_t$ values of 0.94 which is too high. Normalized CVF values in the brain tissues are closer to expected values. In liver tissues, normalization resulted in a remarkable increase in $V_i/V_t$ from 0.80 to 0.91 which is in accord with the tendency of liver cells to contain a high proportion of fat. Second, $V_i/V_t$ values calculated from $[Na]_{tm} - [K]_{tm}$ have relatively large standard deviations, i.e. ±0.03 to ±0.06 whereas normalized CVF values have smaller standard deviations, i.e. ±0.02 to ±0.03. Thus, normalization not only brings the CVF closer to expected values but reduced the scatter of the values.

These data also indicate that normal organs can have very different $[Na]_{tm} - [K]_{tm}$ values. The $[Na]_{tm} - [K]_{tm}$ values varied over a 60 μmol/g (or mM) range from −65 to −4 mM. This finding is important because it establishes that different tissues can be easily differentiated from each other on the basis of their $[Na]_{tm} - [K]_{tm}$ values. This is advantageous for imaging applications. Indeed, imaging apparati can bootstrap each pixel so that $[Na]_t + [K]_t = [Na]_p + [K]_p$.

Four well-established methods are currently available for measuring $[Na]_t$ and $[K]_t$. First, the tissue can be homogenized and then measured with ion-selective microelectrodes. Second, sodium and potassium can be measured by titrimetric methods. Third, atomic absorption spectrophotometry can be used. Fourth, emission spectrophotometry can be used. There are now several highly selective dyes which fluoresce as a function of sodium or potassium ionic concentration. These methods can measure the differences in tissue sodium and potassium concentrations with a precision of better than 5%, based on current technology, and can be readily incorporated into an instrument designed to measure and display values of G* and IVF*, where G* represents the idealized average transmembrane cationic gradient when IVF is constant, and IVF* represents the idealized average intracellular volume fraction when G is constant.

Figure 2:
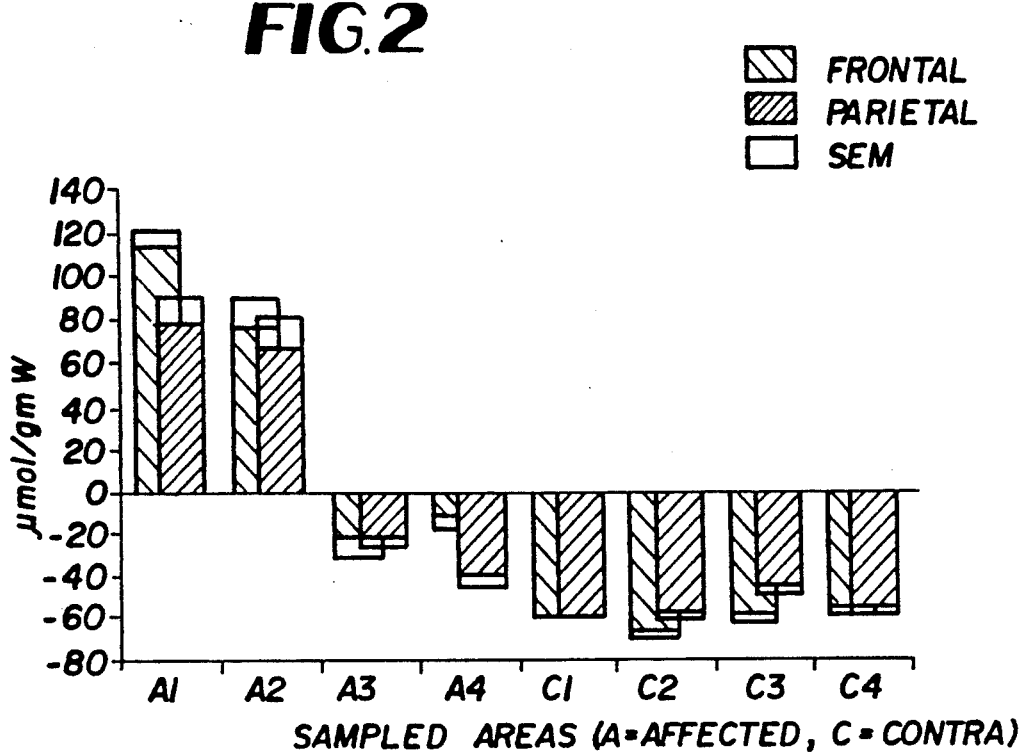
FIG. 2 shows the mean differences in tissue sodium and potassium concentrations in rat brains at 24 hours after middle cerebral artery occlusion. $[Na]_w$ and $[K]_w$ represent wet tissue concentrations of sodium and potassium, respectively, expressed in $\mu$moles per gram wet tissue weight. Concentration values expressed in $\mu$mol/g W units approximate millimolar concentration units since 1 g of wet tissue is approximately 1 ml in volume.
Figure 4:
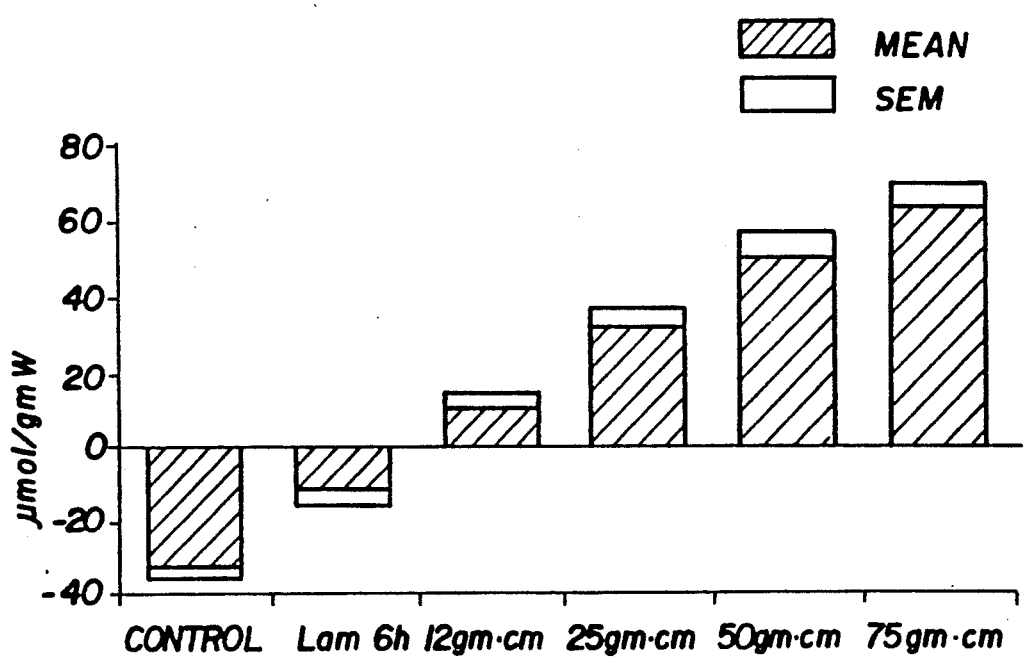
FIG. 4 shows the mean values of $[Na]_w-[K]_w$ in graded spinal cord contusion.

Another method that is easily adapted to the measurements required by the method of the present invention is nuclear magnetic resonance. Most magnetic resonance imaging techniques are based on detecting small changes in tissue hydrogen (predominantly water) or changes in phosphate concentrations. These changes typically do not exceed 5-10 mM in tissue injury, between different types of tissues, or during neural activity. Large changes in the differences between tissue sodium and potassium concentrations occur in injured tissues. This has been shown experimentally to be on the order of 50-200 mM in injured tissues (FIGS. 2-4). Such differences are 5-10 times greater than hydrogen or phosphate concentration changes in the brain and can be readily detectable by magnetic resonance. Thus, magnetic resonance imaging machines can be provided which quantify the difference between tissue sodium and potassium concentrations, reflecting the amount of living cytoplasm in different tissues of the organism, including the brain, heart, kidney, liver, lung, etc.

One method for measuring the concentration of sodium ion in brain tissues is disclosed in U.S. Pat. No. 4,779,619, to Winkler et al., which patent is hereby incorporated by reference. Imaging of sodium content in brain tissue can be done on a conventional nuclear resonance scanner specifically set up for sodium scanning. It is an understood variable of such a system that the resolution obtainable from the image is directly proportional to the signal intensity and static magnetic field of the scanner, and the signal-to-noise is proportional to the square root of the imaging time. Because the expected $[Na]_w - [K]_w$ signal is much greater than expected changes in tissue hydrogen or phosphate concentrations associated with injury, tissue type, or neutral activity, the scan need not be conducted for as long a time period for an image of similar resolution.

Potassium ion NMR studies and combined sodium and potassium NMR studies have been conducted in the prior art. See, for example, Pike, M. M. et al, "Sodium-23 NMR and Potassium-39 NMR Studies of Perfused Rat Hearts Discrimination of Intracellular and Extracellular Ions Using a Shift Reagent," *Biophys. J.*, 48, (1), 1985, 159-174, and Ogino, T. et al, "Sodium-23 and Potassium-39 NMR Studies of Ion Transport in Human Erythrocytes," *Proc. Natl. Acad. Sci. USA*, 82, (4), 1985, 1099-1103. Furthermore, double tuned NMR probes capable of acquiring in-vivo NMR data concurrently from more than one nucleus are known, such as, for example, U.S. Pat. No. 4,742,304 to Schnall et al, and the references cited therein. It is within the skill of those of ordinary skill in the nuclear magnetic resonance spectroscopy art to design an apparatus capable of simultaneously tuning to $^{23}Na$ and $^{39}K$ nuclei. The results can then readily be processed in an associated microprocessor to output the difference in sodium and potassium ion concentrations.

Interpretation of $[Na]_t - [K]_t$ requires some knowledge of $[Na]_e$ and $[K]_e$. Within about two to three hours after an acute event, extracellular cationic levels are approximately equilibrated with plasma levels. $[Na]_e$ and $[K]_e$ can be measured in the tissue with ion-selective microelectrodes. Alternatively, in the case of brain measurement, cerebrospinal fluid can be used to estimate the values of $[Na]_e$ and $[K]_e$ after a period of several hours. Since both plasma and cerebrospinal fluid values of $[Na]_e$ and $[K]_e$ should remain relatively stable, i.e., $\pm 5-10$ mM, one measurement is sufficient in a given operation or experiment. In any event, since the values of $[Na]_t - [K]_t$ generally change by 50-60 mM, the error is relatively small, even if the values of $[Na]_e - [K]_e$ were simply assumed to be normal.

The values of G and IVF are difficult to measure directly by any currently available method (except when the tissue is blood in which IVF is the hematocrit). Measurement of G, for example, requires intracellular cationic measurements. Measurement of IVF requires tracers that are localized to either the intracellular or extracellular compartments, and methods to measure the concentration of the tracer in the extracellular or intracellular space.

One way of overcoming this difficulty is to assume a normal value, i.e., 100 mM, for G. In such a case, $V_i/V_t$ represents the volume of cytoplasm that has not equilibrated with extracellular fluids. The value of $V_i/V_t$ obtained by setting G to normal values is called the idealized intracellular volume fraction, represented as IVF*. Alternately, a normal value of $V_i/V_t$ can be assumed, from which the value of G can be calculated. This assumption would be justified, for example, if the cellular density of the tissue is known to be normal. The value of G when IVF is assumed to be normal is called the idealized cationic gradient, and is represented as G*.

The $[Na]_t - [K]_t$ approach to measuring intracellular volume fraction is superior to tracer methods for a variety of reasons. Because the normal values of $[Na]_t - [K]_t$ are known or can be determined, only measurements made after injury are required. No tracers need be delivered to the tissue of interest, since both sodium and potassium are endogenous to all body tissues. No assumptions or fudge factors are necessary. The method merely requires that intracellular and extracellular fluids be isotonic. The greatest conceivable osmotic or hydrostatic gradient will contribute less than a 2% error to the measurements.

The following non-limiting examples demonstrate the validity and feasibility of the subject method for determining tissue damage.

The data presented below fall into four categories. First, the data show that $[Na]_t - [K]_t$ invariably predicts the locations of infarct sites in rat brains after occlusion of the middle cerebral artery (MCAo). Second, the data show a direct correspondence between the value of $[Na]_t - [K]_t$ and the severity of injury in rat spinal cords after graded contusion injury. Third, $[Na]_t - [K]_t$ measurements were made in brain specimens from several patients; in these data, $[Na]_t$ and $[K]_t$ concentration terms are referred to as $[Na]_w$ and $[K]_w$, since these concentrations were expressed in $\mu$mol/gram wet tissue weight. Fourth, the data show that $[Na]_t - [K]_t$ is an accurate predicter of blood hematocrit and, indeed that $[K]_t$ alone is a reasonable predicter of blood hematocrit.

EXAMPLE 1

Occlusion of the middle cerebral artery, MCAo, in the rat produces a localized infarct in the frontal and parietal cortex. These lesions were studied in 100 rats. $[Na]_w$ and $[K]_w$ were measured in regions at and around the infarct site at 2, 4, 6, 24, 28, and 178 hours after the arterial occlusion. FIG. 1 shows the method used for these determinations. Two 3-mm coronal slices were cut from each rat brain. Eight pieces of tissue were punched from each slice, four from the ischemic and four from the contralateral non-ischemic hemisphere. The tissue was weighed for wet weight, dried, and weighed for dry weight. The tissue was then digested in acid. Aliquots were removed for sodium and potassium measurements. The residue was cooked in a muffle oven and analyzed for sodium, potassium, and calcium by atomic absorption spectroscopy.

Atomic absorption spectroscopy was used to measure the total tissue concentrations of sodium and potassium, i.e., $[Na]_w$ and $[K]_w$. The tissues were sampled from the infarct center in the frontopyriform cortex, shown as area 1; infarct border in the frontoparietal cortex, shown as area 2; beyond the infarct border in the parasagittal cortex, shown as area 3; and the subcortical nucleus, shown as area 4. Without exception, $[Na]_w - [K]_w$ predicted the location and the severity of the infarct.

FIG. 2 shows the mean $[Na]_w - [K]_w$ in the frontal and parietal slices of 24 rats at 24 hours after MCAo. Areas 1 and 2 represent the infarct site, area 3 represents samples taken from the parasagittal cortex, area 4 is from the subcortical nucleus, and areas $C_1$ to $C_4$ are from the contralateral nonischemic hemisphere.

Figure 3A:
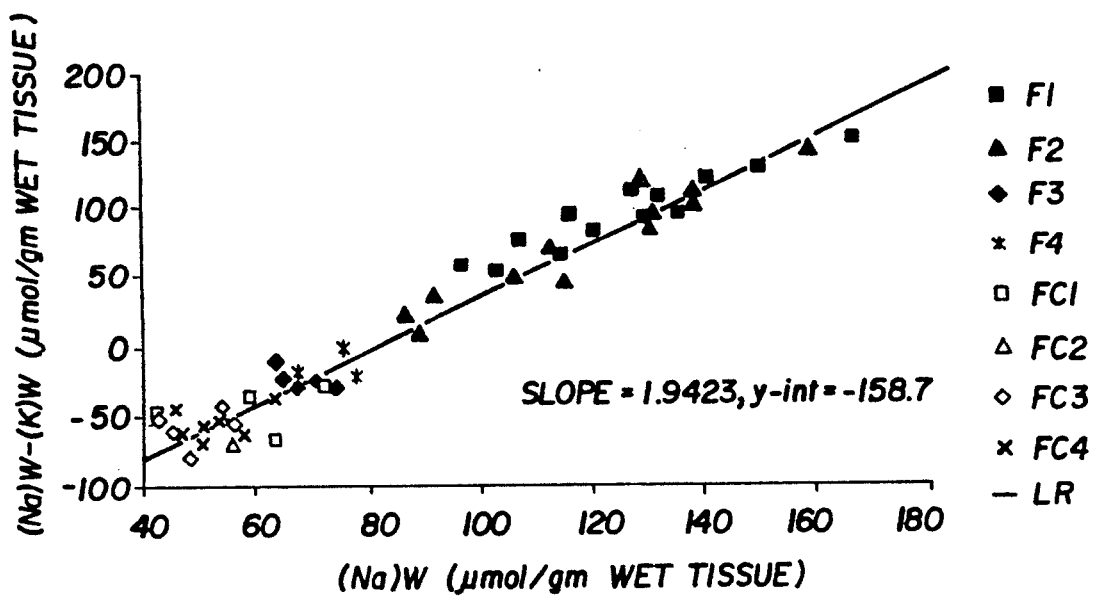
FIGS. 3A and 3B show scatterplots of $[Na]_w-[K]_w$ versus $[Na]_w$ in a frontal cortical slice at 6 and 24 hours after middle cerebral artery occlusion, respectively.
Figure 3B:
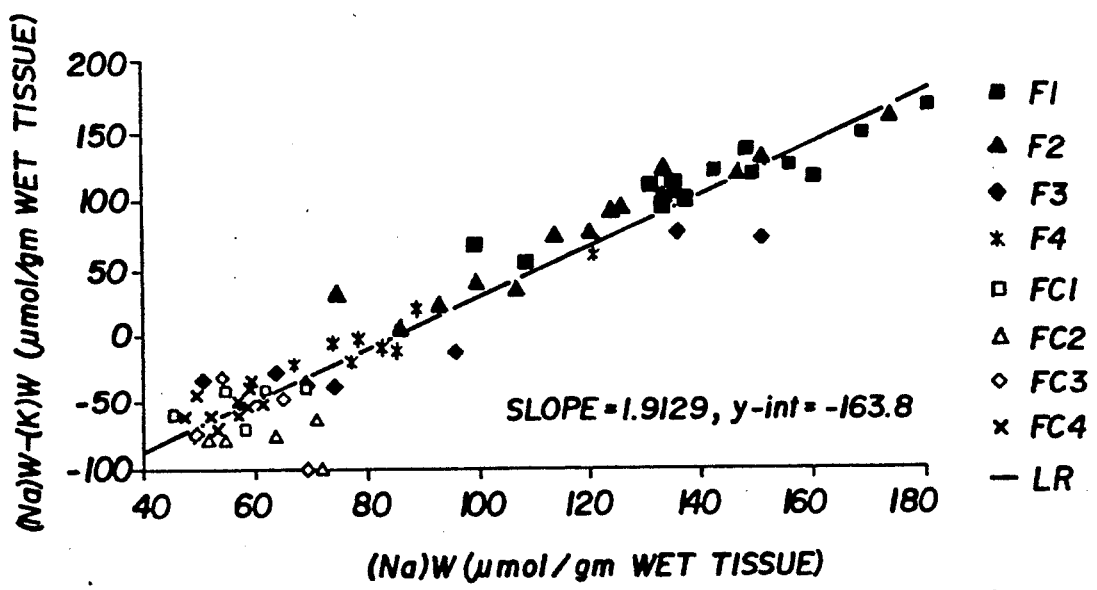

FIGS. 3A and 3B show scatterplots of $[Na]_w - [K]_w$ versus $[Na]_w$ at six and 24 hours, respectively. The filled squares and triangles represent the infarct site. Without exception, all of the data suggest the method is valid for considerable periods of time after the initial tissue injury.

EXAMPLE 2

Dropping a 10 gram weight from a height of 1.25 cm, 2.5 cm, 5.0 cm, and 7.5 cm onto the thoracic spinal cord of the rat produces increasing spinal cord injury. The injury energies are expressed as the product of the weights and heights of the weight drop. The spinal cords were cut into ten 4 mm segments, with one segment centered on the contusion site and the remainder at sequential 4 mm distances from the contused segment. All of the samples were taken and examined at six hours after contusion. There is a linear relationship between the $[Na]_w - [K]_w$ and the impact velocity of the contusion.

FIG. 4 shows the mean values of $[Na]_w - [K]_w$ measured at the impact site at six hours after injury. The small standard errors of the mean and the linear relationship between the injuring energy (gm·cm) and $[Na]_w - [K]_w$ are noteworthy.

It was found in this experiment that changes in tissue sodium, potassium, calcium, and water concentrations were not able to distinguish between injuries that were less than 50 gm·cm apart in energy, i.e., 12 gm·cm versus 25 gm·cm, 25 gm·cm versus 50 gm·cm and 50 gm·cm versus 75 gm·cm. However, $[Na]_w - [K]_w$ was able to segregate each level of injury distinctly and with a high degree of reliability. It should be noted that the range of $[Na]_w - [K]_w$ is from <35 mM to >65 mM, a span of 100 mM. Each mean value represents an average of data from eight separate experiments. The standard errors of mean are also very small. Controls were unoperated animals. This experiment demonstrated that $[Na]_w - [K]_w$ values are the best predictor of spinal cord injury yet encountered, and are superior to $[Na]_w$, $[K]_w$, $[H_2O]_w$, or $[Ca]_w$ alone. Such measurements can be used to distinguish between relatively small differences in time change. Thus, $[Na]_{tm} - [K]_{tm}$ readings can be utilized not only to localize but also quantify spinal cord injury and other types of traumatic tissue damage. Finally, these large $[Na]_{tm} - [K]_{tm}$ changes are present at 6 hours after injury. Thus, early detection and quantification of tissue damage resulting from trauma and ischemia is feasible.

EXAMPLE 3

$[Na]_t - [K]_t$ measurements were conducted in human brain tissue, using samples of brain that were removed in the course of exposing aneurysms. In the four patients tested, there was a correlation between the degrees of clinical deficits related to subarachnoid hemorrhage and the $[Na]_t - [K]_t$ values. While this data is yet still preliminary, the data showed that human brain tissues have cationic concentrations that are similar to the rat brain and $[Na]_w - [K]_w$ analyses suggest similar values of $G^*$ and $IVF^*$. Cerebrospinal fluid measurements of sodium and potassium were very stable, with less than 1% standard deviation among the four patients.

EXAMPLE 4

Samples of fresh blood were obtained from 61 pentobarbital anesthetized Long-Evan's hooded rats (35 mg/kg i.p.) that were being decapitated after thoracic spinal cord injury. Approximately 24 hours before the decapitation, these rats received laminectomies and a 10 g weight was dropped 1.25–7.5 cm onto the spinal cord. The rats were then treated intravenously for 24 hours with a variety of drugs (30 mg/kg methylprednisolone, 0.3 mg/kg nalmefine, 3 mg/kg tirilazad, or 20 ml saline over the 24 hour period. Mixed venous and arterial blood samples (2–3 ml) were collected in Na-free heparinized tubes when the rats were decapitated. Small samples of whole blood were removed for hematocrit determinations in capillary tubes, using standard centrifugation procedures. The tubes of blood were then centrifuged to separate blood and plasma. A 0.1 ml aliquot was taken for serum Na ($[Na]_e$) and K ($[K]_e$) determinations by atomic absorption spectroscopy. The blood was then homogenized and analyzed for total blood Na ($[Na]_t$ and K ($[K]_t$) concentrations. All Na and K concentrations are expressed in mM.

All Na and K determinations were made by atomic absorption spectroscopy. Known volumes (precision of 1%) of plasma and blood samples were placed in porcelain crucibles (Coors), weighed to obtain tissue wet weight (W), dried overnight at 100° C. in a vacuum oven, and then weighed again for tissue dry weight (D). The dried blood was then dissolved in 1 ml of concentrated nitric acid and heated on a hot plate at about 100° C. until dry. After redissolving the residua in 1 ml of nitric acid, a 0.1 ml aliquot was diluted into 9.9 ml of deionized water, and analyzed by acetylene-air flame atomic absorption spectroscopy (AAS) for Na and K at 589.6 nm and 766.5 nm wavelengths. All measurements were bracketed with Na and K standards and confirmed by the method of standard additions to the samples.

Atomic absorption spectroscopy measures the total amount of Na and K in the samples, regardless of ionization state. The measurements do not necessarily indicate ionic activity. We checked a number of samples with ion-selective electrodes and confirmed that the atomic absorption measurements are reasonable reflections of ionic activity measured with ion-selective electrodes. In general, the activities were 2–3% lower than the total tissue ionic measurements but otherwise closely matched the atomic absorption measurements, especially when the ionic concentrations were expressed as a function of fluid volume.

To prevent blood clots, approximately 0.2 ml amounts of heparin solution (Sigma, Inc., St. Louis, Mo.), containing little or no Na and K, were placed in the sample tubes and allowed to dry. Although clotting does not interfere with atomic absorption analyses, it can produce gross errors in hematocrits. Cell lysis can increase $[K]_e$ and lower $[Na]_e$. Samples that were grossly clotted were not used in the analysis. Likewise, whenever there is significant blood cell breakdown, as evidenced by pink plasma due to red blood cell lysis, the blood specimen was not used as lysis can also produce gross errors in hematocrits. Again, however, it does not interfere with the procedure in accordance with the present invention.

To ascertain the accuracy of the methods, repeated measures were made on some of the blood samples for both hematocrit and ionic measurements. All mean values of ionic concentrations are expressed with standard errors of means (sem). Likewise, linear regression analysis yielded slopes and y-intercepts with sem. Statistical analyses were carried with two-tailed t-tests of the means and sem.

Figure 7:
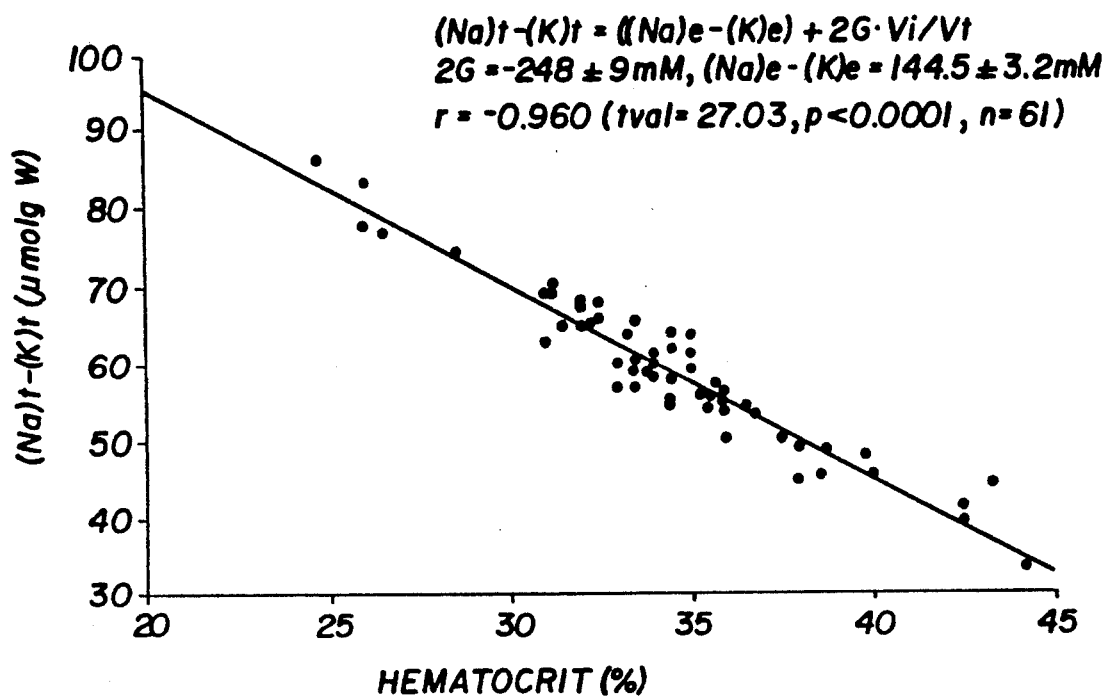
FIG. 7 is a graph showing the relationship of $[Na]_t-[K]_t$ with hematocrit.

The results of the above-described measurements established that $[Na]_t - [K]_t$ correlated significantly with hematocrit (FIG. 7). Linear regression analysis revealed a slope of 248±9 mM (mean±sem) and a y-intercept (Yi) of 144.5±13.2 mM. The correlation coefficient (r) was 0.960 with a t-value of 27.03 (p<0.0001). According to equation (7), the linear regression slope represents 2G, i.e., the average transmembrane gradient of K ions in the blood cells, suggesting that G is −124 mM. This value of G suggests a Nernst potential of approximately −90 mV, close to the reported literature value of K Nernst potentials across blood cell membranes. The y-intercept represents $[Na]_e - [K]_e$ and was 144.5±2.3 mM (mean±sem). This value is very close to the actual measured plasma $[Na]_e - [K]_e$ values in the blood samples, i.e., 144.0±0.7 mM. These observations strongly support the initial assumption that intracellular and extracellular fluids are isotonic in the derivation of equation 7. If this assumption were incorrect, neither the slope nor the y-intercept would be so consistent. The scatter represents measurement error.

Figure 8:
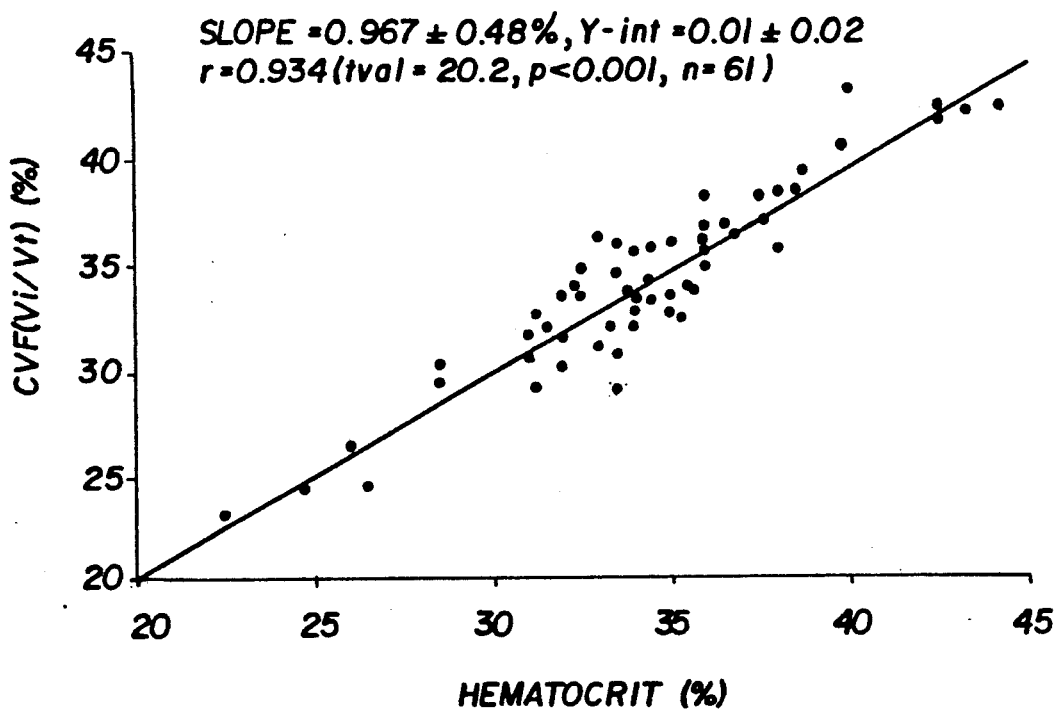
FIG. 8 is a graph showing the relationship of cell volume fraction with hematocrit.

Using the measured values of $[Na]_t - [K]_t$ and $[Na]_e - [K]_e$ and substituting −124 mM for G, the cellular volume fraction (CVF) or $V_i/V_t$ was calculated from equation (7). The calculated values of $V_i/V_t$ correlated closely with hematocrit, as shown in FIG. 8. The slope of the relationship approached unity and the y-intercept did not differ significantly from the origin. The correlation coefficient was 0.934 with a highly significant t-value of 20.2 (p<0.001). Thus, $V_i/V_t$ values calculated from $[Na]_t - [K]_t$ and $[Na]_e - [K]_e$ predicts hematocrit in a quantitative fashion. The standard errors of the correlation are slightly greater than those associated with repeated measures of hematocrit.

Figure 9:
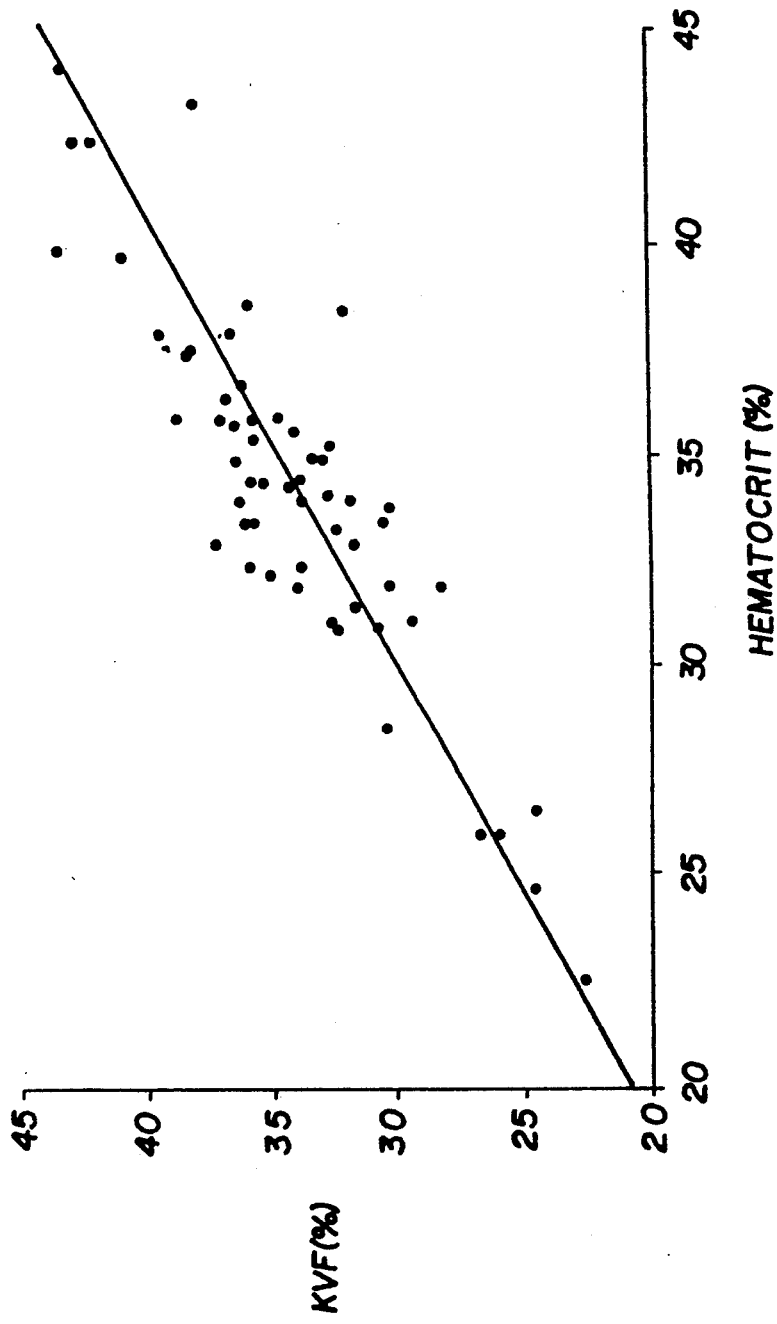
FIG. 9 is a graph showing the potassium volume fraction (KVF) versus hematocrit. KVF was calculated from $([K]_t-5)/124$.

Linear regression analysis indicates that $(5 - [K]_t)/124$ (from equation (10)) is also highly predictive of hematocrit. Cell volume fractions calculated from $([K]_e - [K]_t)/G$ are called "potassium volume fractions" (KVF) to distinguish it from $V_i/V_t$ calculated using measured values of $[Na^+]_e - [K^+]_e$. The slope of $([K]_e - [K]_t)/G$ versus hematocrit approaches unity and the y-intercept is not significantly different from zero, as can be seen from FIG. 9. The correlation is not as good as $[Na]_t - [K]_t$. Nevertheless, the correlation is significant and only slightly outside the limits of accuracy that one normally achieves with careful hematocrit measurements. In repeated measures of hematocrits from the same blood samples, standard errors of 2–3 hematocrit units, which represent as much as 10% error in hematocrits in the range of 20–30%, are often obtained. In contrast, repeated measures of $[Na]_t - [K]_t$ were seldom off by more than 1–2% of the mean values. Volume measurements with adjustable micropipettes were accurate only to 1%.

These studies indicate the feasibility of utilizing $[Na]_t - [K]_t$ to estimate blood hematocrit. In rats with a wide range of hematological states, hematocrit was predictable with $[Na]_t - [K]_t$ within one or two units over a range of 20–45% hematocrit. Moreover, linear regression analysis of the relationship between $[Na]_t - [K]_t$ and hematocrit indicated a slope of 248 mM and a y-intercept of 145 mM. These values confirm the theoretical prediction that the slope of $[Na]_t - [K]_t$ and hematocrit should produce a slope that is twice the K gradient across cell membranes and a y-intercept equal to the difference in measured extracellular Na and K concentrations. The slope and y-intercept fit well with known published values of transmembrane K gradients and measured plasma ionic Na and K concentrations in blood samples.

Assuming that the transmembrane potassium gradient (G) is −124 mM, the cellular volume fraction can be estimated from measured values of $[Na]_t - [K]_t$ and $[Na]_e - [K]_e$. These calculated cellular volume fraction values predicted hematocrit with surprising accuracy (correlation coefficient of 0.934, t-value of 20.2, p-value of <0.001), suggesting that the assumption of 124 mM for the transmembrane K gradient is reasonable and applies over a wide range of hematological conditions. Cellular volume fractions calculated from the distribution of Na and K therefore accurately reflect hematocrits.

The $[Na]_t - [K]_t$ theory can be further extended by simplifying the relationship between $[Na]_t - [K]_t$ and hematocrit to only one variable, $[K]_t$, by assuming normal values of $[K]_e$ and G. While the data indicates that these assumptions are reasonable and do not systematically vary under a wide range of hematological conditions, they undoubtedly contribute to increased scatter of the data. For example, measured plasma $[K]_e$ values varied from 3.5 to 6.5 mM although such changes constitute <5% of the scatter of $[Na]_e - [K]_e$ values measured. The $V_i/V_t$ values calculated from such assumptions nevertheless predicted hematocrit, although less well than $[Na]_t - [K]_t$ or $V_i/V_t$, probably due to scatter of G values.

Use of $[Na]_t - [K]_t$ to estimate hematocrit has several advantages. First, it can be applied to clotted and lysed blood. Once the blood is removed from the body, $[Na]_t$ and $[K]_t$ cannot degrade or change. The only major source of error would be drying of the blood sample.

But even that problem can be overcome to a point by assuming normal blood tonicity and normalizing the calculated values so that $[Na]_t-[K]_t$ is equal to 150 mM. Second, $[Na]_t-[K]_t$ can be easily measured with electrodes in a compact and portable instrument. Third, and not least, $[Na]_t+[K]_t$ is an estimate of the blood tonicity and is a measure of dehydration, an important variable in the interpretation of hematocrit.

The $[Na]_t-[K]_t$ approach to measuring hematocrit has one potential weakness. The slope of relationship of $[Na]_t-[K]_t$ with hematocrit depends on G, the ionic gradient across blood cell membranes. While the data of the present example indicates that G appears relatively constant in rat blood over a wide range of post-operative conditions, this would have to be established in human blood in different disease states. This can be relatively easily done by measuring $[Na]_t-[K]_t$, $[Na]_e-[K]_e$ and hematocrit, substituting into equation (7) and solving for G. Note that G is not easily measured by other means and G represents a clinical hematological parameter that may be useful diagnostically.

There are many applications of the $[Na]_t-[K]_t$ method of measuring tissue damage. Although much of the data presented above emphasizes brain and spinal cord tissues, as well as blood, the method is applicable to peripheral tissues such as heart, lungs, liver, kidney, muscles, and intestines. The same theoretical principles apply, and peripheral tissues do not have the complicating factor of the blood brain barrier retarding equilibration between interstitial and vascular fluids.

The method of measurement according to the present invention can be used with instrumentation for use both in the operating room and the laboratory. The equipment for monitoring tissue vitality is dedicated to measuring IVF* and G*, with built-in microprocessor control of the measurements and calculation programs which display the values in the bar-graph, e.g., with light-emitting diodes.

The method of the present invention is also useful in conjunction with instrumentation to measure IVF* and G* in connection with the surgical instrument used to remove tissues. A Cavitron ultrasonic surgical aspirator is used for rapid removal of tissues. Using the method of the present invention, instrumentation to measure IVF* and G* permits the surgeon to evaluate the degree to which the removed tissue has been injured and when normal tissues are being removed.

The method of the present invention is also useful in the detection of cancerous tissues as they are being removed. Such tissues should have a different IVF* and G*, as compared to healthy tissues. During surgery, instantaneous measurements are taken of these values, so that the surgeon can ensure complete removal of tumor tissue without removal of excessive amounts of healthy tissue.

The method of the present invention is particularly useful when used in conjunction with a Cavitron ultrasonic surgical aspirator (CUSA), made by Cavitron division of Pfizer. The CUSA comprises a hand-held ultrasonic vibrating probe which emulsifies, aspirates, and irrigates tissue which it contacts. The instrument can be modified to include a means for measuring sodium and potassium ion concentration in the tissue slurry emanating from the probe. Dilution of tissue fluids by irrigation fluids can be corrected for by adding a tracer to the irrigation fluid. For example, when using atomic absorption spectroscopy for detection of $[Na]_t-[K]_t$, a tracer, such as gadolinium, is added to the irrigation fluid. Alternatively, the tissue removed by the CUSA is directed to another means for measuring tissue sodium and potassium, such as an atomic absorption spectrophotometer, a flame photometer, an ionic titrator, or a nuclear magnetic resonance spectroscope. For use in an operating room, the atomic absorption spectrophotometer may be equipped with an electrical burner, since flames are forbidden in operating rooms. Another means for measuring the sodium and potassium concentrations in the tissue slurry emanating from the probe are potassium and sodium sensitive microelectrodes in line with the tubing carrying the tissue fluids.

Figure 5:
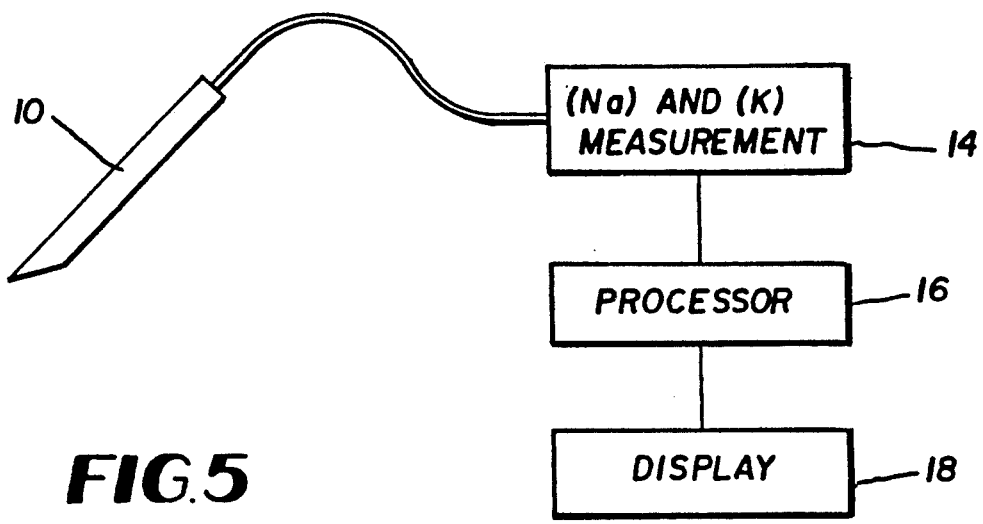
FIG. 5 is a schematic diagram showing an apparatus in accordance with the present invention including an ultrasonic surgical aspirator.

A schematic representation of such an apparatus using an ultrasonic surgical aspirator is shown in FIG. 5. The aspirator 10 is connected via a tube 12 to a device 14 for measurement of the sodium ion and potassium ion concentrations of the excised tissue passing through the tube. The measurement may be continuous, as by means of sodium and potassium ion selective electrodes, or by batch processing, as by means of atomic absorption spectrophotometry. The measured values of sodium and potassium ion concentrations are then fed to a processor 16, which may be a digital computer. In processor 16 the value for the potassium ion concentration is subtracted from the value for the sodium ion concentration and the value for the difference is sent to a display 18 where it may be digitally or graphically displayed. The display 18 may include a constant comparison with a known value for normal tissue and may include an alarm, such as an audible warning signal, when the value from the processor 16 approaches the value for normal tissue, thereby indicating that undamaged tissue or non-cancerous tissue is inadvertently being excised by aspirator 10.

Magnetic resonance imaging is particularly well suited to the method of the present invention because sodium and potassium are detectable via nuclear magnetic resonance. Both sodium and potassium have odd-numbered nuclear weights and are present in high concentrations in tissues. Multiply tuned NMR probes are known in the art, such as U.S. Pat. No. 4,742,304 to Schnall et al, discussed above. Such probes may be used to measure in vivo at least two different nuclei. A suitably tuned probe can simultaneously measure sodium and potassium ion concentration and the processor typically included with all NMR machines can be programmed to determine the difference in the measured [Na] and [K] and image the area based on different colors for different calculated values of this difference. Such images would show tumors or lesions in a different color from the surrounding tissue and tissue of different organs in different colors from one another because in non-necrotic tissues in which the average intracellular volume fraction is substantially constant, the $[Na]_t-[K]_t$ value will directly relate to G* which differs for different tissue types.

Figure 6:
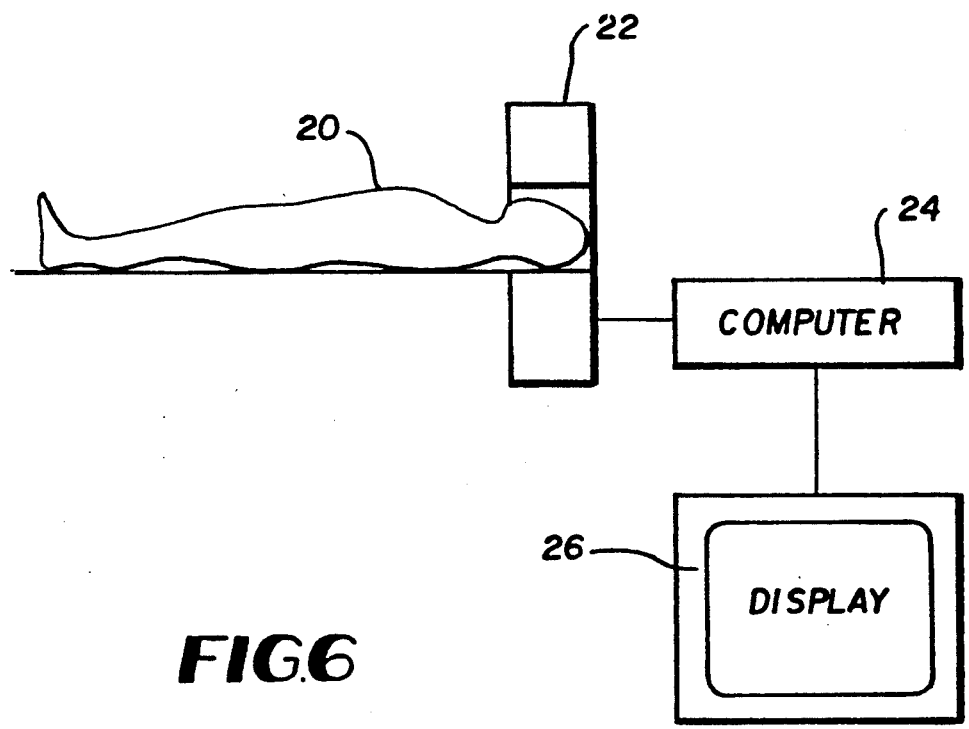
FIG. 6 is a schematic diagram showing an apparatus in accordance with the present invention including a scanning NMR spectroscope.

A schematic representation of such an apparatus using NMR is shown in FIG. 6. The magnet 22 of a scanning NMR spectroscope may be disposed about the head of a patient 20 with an appropriately placed double-tuned probe (not shown) set to the resonance of $^{23}$Na and $^{39}$K. The values obtained are sent to a computer 24 where the $[Na]_t-[K]_t$ values are calculated for each area of the brain being scanned and the results are sent to a display 26 where the resultant image may be displayed. Each area of different $[Na]_t-[K]_t$ value may be displayed in a different color so as to clearly show the areas of different tissue type or the position of lesions or tumors.

Alternatively, fluorescent dyes can be used to determine $[Na]_t - [K]_t$. Fluorescent dyes are now available which will selectively fluoresce when bound to a particular ion, i.e., sodium sensitive dyes and potassium sensitive dyes. As the dyes can be selected such that they will fluoresce at different wavelengths, they may be simultaneously administered to measure sodium and potassium concentrations concurrently. The fluorescent dyes are injected into the tissue, and the dyes may be excited with a laser and measured by emission spectroscopy to determine the amount of sodium and potassium present in the tissue.

The method of the present invention is also useful for measuring neural activity in undamaged brain tissue. It is known that movements of sodium and potassium generate the electrical currents necessary for brain activity. While one might think that nuclear magnetic resonance imaging could not be used to measure neural activity because it takes many minutes to resolve signals by averaging, due to the high concentrations of $[Na]_t$ and $[K]_t$ and the fact that the present method requires measurement only of the difference in ion concentrations, and not absolute values, the method will be much more sensitive and will require less time to resolve the signals.

The neural activity is measured by determining $[Na]_t - [K]_t$, and comparing to normal values for G and IVF. The differences in $[Na]_t - [K]_t$ reflect differences in neural activity. This method requires measuring differences of ion concentrations, rather than absolute ion concentrations, so that measurements can be taken rapidly and activities plotted for time.

Figure 10:
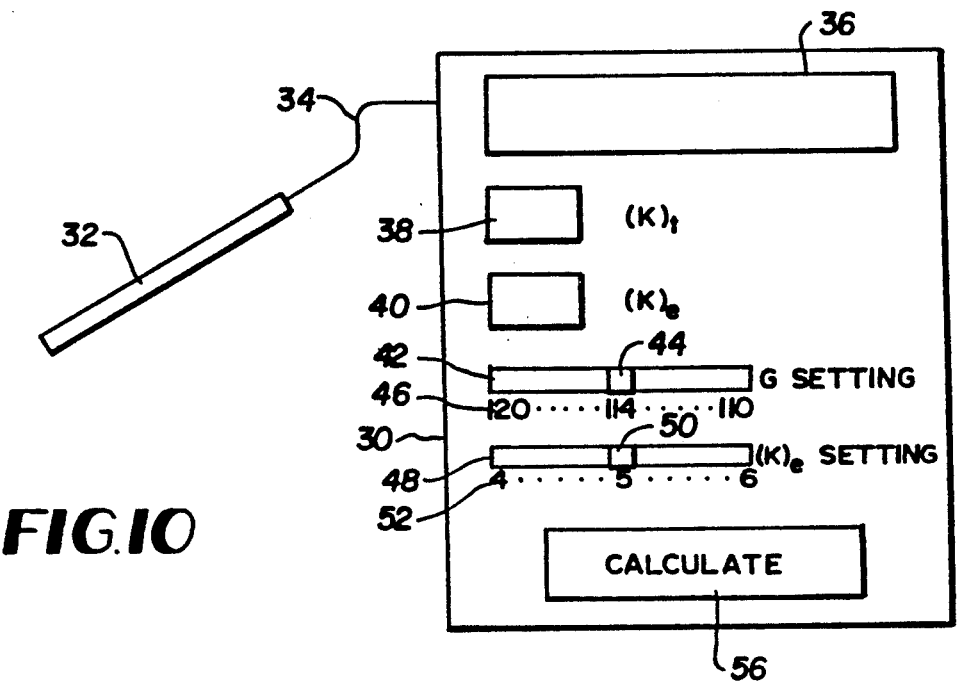
FIG. 10 is a schematic diagram showing an apparatus in accordance with the present invention for measuring hematocrit.

The method for determining hematocrit in accordance with the present invention may be accomplished by means of a simple portable apparatus which will allow an easy and accurate determination of hematocrit without the necessity of dealing with capillary tubes or centrifuge machines. FIG. 10 is a schematic diagram of such an apparatus. The apparatus includes a calculator 30 connected to a postassium ion selective electrode 32 by means of a cord 34. When such an electrode 32 is immersed in a solution of fixed volume, it will determine the pK, from which the calculator 30 can calculate and input into its memory the potassium ion concentration ($[K]$). Such potassium selective electrodes are presently commercially available.

In the simple embodiment of FIG. 10, the calculator 30 includes a display 36. Thus, when the electrode 32 is placed in a fixed volume of liquid, the measured value of $[K]$ is displayed in display 36. If the liquid is homogenized whole blood, the button 38 is depressed, when the displayed value is stabilized, in order to input that value into a memory location of the calculator 30.

The calculator 30 also includes a button 40 which is depressed when a stable value is displayed for $[K]_e$, i.e., when the probe is measuring the potassium concentration of the extracellular plasma. A slide setting 42 is provided in order to set the assumed value for G. A slider 44 may be moved to the desired setting for G. It is normally disposed at a setting of 124 but if other information leads to a conclusion that the assumed value of G should be somewhat higher or lower, the slide 44 can be moved to the appropriate value as displayed therebelow 46. Similarly, the calculator also includes a slide setting 48 and a slider 50 and display 52 for setting an assumed $[K]_e$. It is normally set to the normal value of 5 but can be varied if desired.

Finally, the calculator includes a calculate button 56. After the appropriate input has been set, the calculate button instructs the calculator to calculate the cellular volume fraction in accordance with the equations discussed above. The results are displayed in display 36.

Thus, the apparatus of FIG. 10 permits two ways of determining hematocrit. If a measured value of $[K]_t$ is input by inserting electrode 32 into a sample of homogenized or lysed whole blood and pressing button 38 when the displayed results are stablized, and the calculate button 56 is immediately pressed, the hematocrit will be determined in accordance with equation (10) using the settings for G and $[K]_e$ set on the slide switches 42 and 48. However, if prior to depression of the calculate button 56 a measured value of $[K]_e$ is determined by placing the electrode 32 into a sample of extracellular blood, or plasma, and after the display has stabilized depressing button 40, then depression of the calculate button 56 will permit determination of hematocrit based upon the measured values of $[K]_t$ and $[K]_e$ and the setting of G set forth on the slide set 42.

Figure 11:
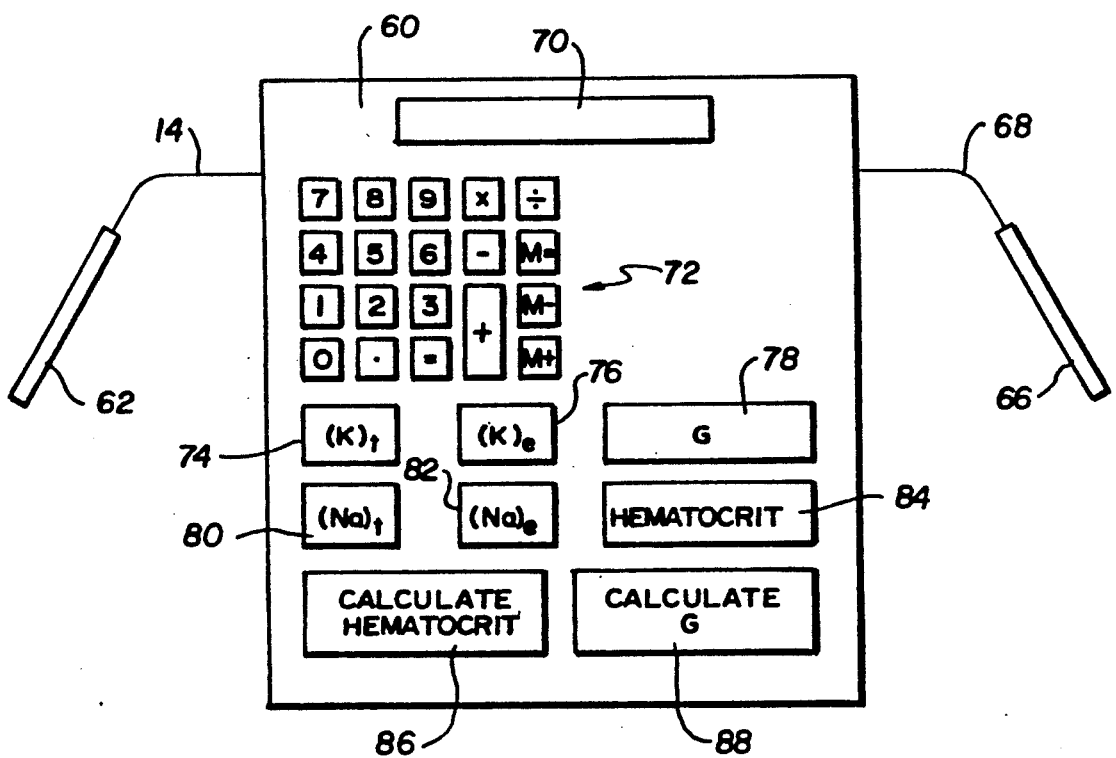
FIG. 11 is a schematic diagram showing an alternative embodiment of an apparatus in accordance with the present invention for measuring hematocrit, which can also measure the cationic gradient across the blood cell membranes.

Another embodiment of a hematocrit determination calculator which can also calculate the value of G is shown in FIG. 11. The device of FIG. 11 is a calculator 60 having a potassium selective electrode 62 connected thereto by a cord 64 as well as a sodium selective electrode 66 connected thereto by a cord 68. A standard calculator key pad 72 is present for entry of information. Key 74 is similar to key 38 discussed above for FIG. 10 in that it is depressed in order to enter into memory the displayed value of $[K]_t$. The value of $[K]_t$ appearing in the display 70 may either be that value measured by the electrode 62 or may be entered by the key pad 72. The same is true with respect to keys 76, 80 and 82 for entry into memory of values for $[K]_e$, $[Na]_t$ and $[Na]_e$, respectively. Measured values of $[Na]_t$ are determined by the sodium selective electrode 66. In the embodiment of FIG. 11, the assumed value for G is input by means of the keypad 72 rather than a slide setting 42 as in the embodiment of FIG. 10. The desired value of G is entered by the keypad 72 and then button 78 is pushed to enter this value into memory. Optionally, the calculator can have a default value of G set at 124 which is entered when G is pushed with 0 in the display 70. By means of button 84, a value of hematocrit measured by some other technique can be entered by means of the keypad 72. This is used in the calculation of G in accordance with equation 12.

When values of $[K]_t$, $[K]_e$ and G are entered via buttons 74, 76 and 78, the button 86 may then be pushed in order to calculate the hematocrit and display the result in the display window 70. When values for all of $[K]_t$, $[K]_e$, $[Na]_t$, $[Na]_e$, and hematocrit are entered, G may be calculated by pressing button 88 and the result will be displayed in display 70. The microprocessor (not shown) in the calculator 60 is preset to perform the appropriate calculations.

It should be understood that the embodiments shown in FIGS. 10 and 11 are merely schematic and those of ordinary skill in the art will be able to produce a variety of designs of apparatus for accomplishing the various functions required. Devising appropriate microprocessor chips for such calculators is well within the skill of those of ordinary skill in the art and need not be detailed here. Sodium and potassium selective electrodes are commercially available.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for quantifying cellular damage in a tissue sample, comprising:
   measuring average sodium ion concentration in the entire tissue sample ($[Na]_t$);
   measuring average potassium ion concentration in the entire tissue sample ($[K]_t$);
   obtaining a value equal to $[Na]_t - [K]_t$; and
   comparing said value to the value of $[Na]_t - [K]_t$ in normal tissue,
   whereby the degree of deviation from normal values is a quantitative indication of cellular damage.

2. The method according to claim 1, wherein the tissue is brain tissue.

3. The method according to claim 1, wherein the sodium and potassium ion concentrations are measured using nuclear magnetic resonance spectroscopy.

4. The method according to claim 1, wherein the sodium and potassium ion concentrations are measured by atomic absorption or emission spectrophotometry.

5. The method according to claim 1, wherein the sodium and potassium ion concentrations are measured by ion-selective electrodes.

6. A method according to claim 1, wherein said measured sodium ion concentration is $[Na]_{tm}$ and said measured potassium ion concentration is $[K]_{tm}$ and further including, prior to said obtaining step, calculating normalized values of sodium ion concentration ($[Na]_t$) and potassium ion concentration ($[K]_t$) by:
   measuring the sodium ion concentration in a blood plasma sample ($[Na]_p$);
   measuring the potassium ion concentration in a blood plasma sample ($[K]_p$); and
   multiplying the measured values of $[Na]_{tm}$ and $[K]_{tm}$ by a proportionality factor equal to $([Na]_{tm})/([Na]_p+[K]_p)$ to obtain normalized $[Na]_t$ and $[K]_t$.

7. A method for determination of kind of tissue, comprising:
   measuring sodium ion concentration in the total tissue sample ($[Na]_t$);
   measuring potassium ion concentration in the total tissue sample ($[K]_t$);
   obtaining a value equal to $[Na]_t - [K]_t$; and
   comparing said value to the value of $[Na]_t - [K]_t$ in tissue of known type,
   whereby obtaining a value equal to that of tissue of known kind is an indication that the tissue sample comprises tissue of that known kind.

8. The method according to claim 6, wherein the sodium and potassium ion concentrations are measured using nuclear magnetic resonance spectroscopy.

9. The method according to claim 6, wherein the sodium and potassium ion concentrations are measured by atomic absorption or emission spectrophotometry.

10. The method according to claim 6, wherein the sodium and potassium ion concentrations are measured by ion-selective electrodes.

11. A method according to claim 6, wherein said measured sodium ion concentration is $[Na]_{tm}$ and said measured potassium ion concentration is $[K]_{tm}$ and further including, prior to said obtaining step, calculating normalized values of sodium ion concentration ($[Na]_t$) and potassium ion concentration ($[K]_t$) by:
   measuring the sodium ion concentration in a blood plasma sample ($[Na]_p$);
   measuring the potassium ion concentration in a blood plasma sample ($[K]_p$); and
   multiplying the measured values of $[Na]_{tm}$ and $[K]_{tm}$ by a proportionality factor equal to $([Na]_{tm}+[K]_{tm})/([Na]_p+[K]_p)$ to obtain a normalized $[Na]_t$ and $[K]_t$.

12. A method for monitoring neural activity in an undamaged portion of brain tissue, comprising:
   measuring average a sodium ion concentration in the portion of brain tissue being studied ($[Na]_t$) at predetermined intervals of time;
   measuring average potassium ion concentration in the portion of brain tissue being studied ($[K]_t$) at the same predetermined intervals of time;
   obtaining a value equal to $[Na]_t - [K]_t$ at each said time interval; and
   comparing said values obtained over time,
   whereby variation of said values over time is an indication of neural activity in the brain tissue being studied.

13. The method according to claim 12, wherein the sodium and potassium ion concentrations are measured using nuclear magnetic resonance spectroscopy.

14. A method according to claim 12, wherein said measured sodium ion concentration is $[Na]_{tm}$ and said measured potassium ion concentration is $[K]_{tm}$ and further including, prior to said obtaining step, calculating normalized values of sodium ion concentration ($[Na]_t$) and potassium ion concentration ($[K]_t$) by:
   measuring the sodium ion concentration in a blood plasma sample ($[Na]_p$);
   measuring the potassium ion concentration in a blood plasma sample ($[K]_p$); and
   multiplying the measured values of $[Na]_{tm}$ and $[K]_{tm}$ by a proportionality factor equal to $([Na]_{tm}+[K]_{tm})/([Na]_p+[K]_p)$ to obtain a normalized $[Na]_t$ and $[K]_t$.

15. A method for determining the volume fraction of cells in a tissue sample, comprising:
   measuring potassium ion concentration or total potassium weight present in the tissue sample ($[K]_t$);
   measuring or assuming extracellular potassium ion concentration ($[K]_e$); and
   using a predetermined value for the ionic gradient across cell membranes (G) in the tissue sample, calculating cell volume fraction ($V_i/V_t$), using the formula $V_i/V_t = ([K]_e - [K]_t)/G$.

16. A method in accordance with claim 15, wherein said tissue sample is a blood sample and said volume fraction of cells in the blood sample is the hematocrit, and wherein said step of measuring or assuming $[K]_e$ comprises measuring the potassium ion concentration or the total potassium weight present in the cell-free blood plasma ($[K]_p$) and using said value of $[K]_p$ as $[K]_e$.

17. An apparatus for determining and displaying a value representative of the amount of cellular damage in a tissue sample or the tissue type of a non-necrotic tissue sample, comprising:
   first measuring means for measuring the total tissue sodium ion concentration in the tissue sample;

second measuring means for measuring the total tissue potassium ion concentration in the tissue sample;

processor means for subtracting the measured value of potassium ion concentration obtained from said second measuring means, from the measured value of sodium ion concentration obtained from said first measuring means, to obtain a value for the calculated difference; and display means for displaying the calculated difference obtained by said processor means.

18. An apparatus in accordance with claim 17, further including removal means for removing a tissue sample from a source of tissue and delivering the tissue to said first and second measuring means.

19. An apparatus in accordance with claim 17, wherein said first and second measuring means include an atomic absorption or emission spectrophotometer.

20. An apparatus in accordance with claim 17, wherein said first and second measuring means include a nuclear magnetic resonance spectrometer with a probe double tuned to $^{23}$Na and $^{39}$K.

21. An apparatus in accordance with claim 17, wherein said first and second measuring means include sodium and potassium ion sensitive electrodes.

22. An apparatus in accordance with claim 18, wherein said removal means comprises a surgical aspirator.

23. An apparatus for determining the volume fraction of cells in a tissue sample, comprising:

potassium measurement means for determining the total potassium content or potassium ion concentration of a tissue or fluid sample;

calculator means connected to said potassium measurement means, for calculating cellular volume fraction from the values obtained by said potassium measurement means; and output means connected to said calculator means, for outputting the calculated values of cellular volume fraction.

24. An apparatus in accordance with claim 23 for determining the cellular volume fraction (hematocrit) in a blood sample wherein said potassium measurement means is for determining the total potassium content or potassium ion concentration of a whole blood or cell-free plasma sample.

25. An apparatus in accordance with claim 24 and further including sodium measurement means for determining the total sodium content or potassium ion concentration of a whole blood or cell-free plasma sample and wherein said calculator means is further connected to said sodium measurement means and is further for calculating cellular volume fractions from the values obtained by said potassium measurement means and said sodium measurement means.

26. An apparatus in accordance with claim 24 which can also determine the value of blood cell membrane ionic gradient (G), further including sodium measurement means, connected to said calculator means, for determining the total sodium content or sodium ion concentration of a blood or plasma sample, wherein said calculator means is also for calculating G from the values obtained by said potassium measurement means and said sodium measurement means, and wherein said output means is further for outputting the calculated value of G.

27. An apparatus in accordance with claim 23 and further including sodium measurement means for determining the total sodium content or potassium ion concentration of a tissue or fluid sample and wherein said calculator means is further connected to said sodium measurement means and is further for calculating cellular volume fractions from the values obtained by said potassium measurement means and said sodium measurement means.

28. An apparatus in accordance with claim 27, wherein said sodium measurement means comprises a sodium selective electrode and wherein said potassium measurement means comprises a potassium selective electrode.

29. An apparatus in accordance with claim 27, wherein said calculator means and said output means are packaged in a single portable calculator and wherein said sodium and potassium measurement means are sodium and potassium ion selective electrodes, respectively, each of which are directly connected to said calculator.

30. An apparatus in accordance with claim 23 wherein said potassium measurement means comprises a potassium selective electrode.

31. An apparatus in accordance with claim 23 wherein said output means is for displaying the calculated values of cellular volume fraction.

32. An apparatus in accordance with claim 23, which can also determine the average Na and K gradient across cellular membranes (G) in tissues which have been removed from the body, further including sodium measurement means, connected to said calculator means, for determining the total sodium content or sodium ion concentration of a tissue or fluid sample, wherein said calculator means is also for calculating G from the values obtained by said potassium measurement means and said sodium measurement means, and wherein said output means is further for outputting the calculated value of G.

33. An apparatus in accordance with claim 32, wherein said calculator means further includes input means for inputting estimated or assumed values and said calculator means is further for calculating G from the values obtained by said potassium measurement means and/or said sodium measurement means as well as from values inputted through said input means.

34. An apparatus in accordance with claim 23 which can also determine the average Na and K gradient across cellular membranes (G) in tissues which have been removed from the body, further including input means connected to said calculator means, for inputting estimated or assumed values, wherein said calculator means is also for calculating G from the values obtained by said potassium measurement means and from values inputted through said input means, and wherein said output means is further for outputting the calculated value of G.

35. An apparatus in accordance with claim 23, wherein said calculator means and said output means are packaged in a single portable calculator and wherein said potassium measurement means is a potassium ion selective electrode directly connected to said calculator.

36. A method for measuring the average Na and K gradient across cellular membranes (G) in tissues that have been removed from the body, comprising:

measuring or estimating the cell volume fraction ($V_i/V_t$) of the tissue sample;

measuring the potassium ion concentration in the tissue sample ($[K]_t$);

measuring the sodium ion concentration in the tissue sample ($[Na]_t$);

measuring or assuming a value of extracellular potassium ion concentration ($[K]_e$);

measuring or assuming a value of extracellular sodium ion concentration ($[Na]_e$); and calculating G using the formula:

$$G = (([Na]_t - [K]_t) - ([Na]_e - [K]_e))/2 \cdot (V_i/V_t).$$

* * * * *